(12) United States Patent
Gascon et al.

(10) Patent No.: US 11,278,872 B2
(45) Date of Patent: Mar. 22, 2022

(54) INDIUM-BASED CATALYSTS AND PRE-CATALYSTS

(71) Applicant: King Abdullah University of Science and Technology, Thuwal (SA)

(72) Inventors: Jorge Gascon, Thuwal (SA); Anastasiya Bavykina, Thuwal (SA); Irina Yarulina, Thuwal (SA); Lieven Gevers, Thuwal (SA); Samy Ould-Chikh, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 16/771,864

(22) PCT Filed: Dec. 18, 2018

(86) PCT No.: PCT/IB2018/060288
§ 371 (c)(1),
(2) Date: Jun. 11, 2020

(87) PCT Pub. No.: WO2019/123278
PCT Pub. Date: Jun. 27, 2019

(65) Prior Publication Data
US 2021/0178368 A1    Jun. 17, 2021

Related U.S. Application Data

(60) Provisional application No. 62/654,939, filed on Apr. 9, 2018, provisional application No. 62/599,978, filed on Dec. 18, 2017.

(51) Int. Cl.
*B01J 23/825*  (2006.01)
*B01J 35/02*  (2006.01)
(Continued)

(52) U.S. Cl.
CPC .......... *B01J 23/825* (2013.01); *B01J 35/023* (2013.01); *B01J 35/08* (2013.01); *B01J 35/1014* (2013.01);
(Continued)

(58) Field of Classification Search
CPC ........ B01J 23/825; B01J 35/023; B01J 35/08; C07C 29/156; C07C 31/04
See application file for complete search history.

(56) References Cited

U.S. PATENT DOCUMENTS

| | | | |
|---|---|---|---|
| 4,323,482 A | | 4/1982 | Stiles et al. |
| 4,487,851 A | * | 12/1984 | Heyward ................. B01J 23/08 518/728 |

(Continued)

FOREIGN PATENT DOCUMENTS

WO    2017118572 A1    7/2017

OTHER PUBLICATIONS

Invitation to Pay Additional Fees and, Where Applicable, Protest Fee for PCT/IB2018/060288 dated May 15, 2019.
(Continued)

*Primary Examiner* — Jafar F Parsa
(74) *Attorney, Agent, or Firm* — Billion & Armitage

(57) ABSTRACT

Embodiments of the present disclosure describe pre-catalysts comprising including one or more of indium oxide, indium hydroxide, indium oxyhydroxide, an active oxide, and a refractory oxide. Embodiments of the present disclosure also describe method of making pre-catalysts based on one or more of impregnation, precipitation or co-precipitation, ball milling, and metal-organic framework (MOF)-mediated synthesis. Embodiments of the present disclosure further describe methods of activating pre-catalysts and synthesizing one or more of methanol and olefins using catalysts obtained from the pre-catalysts.

10 Claims, 27 Drawing Sheets

(51) Int. Cl.
*B01J 35/08* (2006.01)
*B01J 35/10* (2006.01)
*B01J 37/00* (2006.01)
*B01J 37/02* (2006.01)
*B01J 37/03* (2006.01)
*B01J 37/18* (2006.01)
*C07C 29/156* (2006.01)

(52) U.S. Cl.
CPC ....... *B01J 35/1038* (2013.01); *B01J 35/1061* (2013.01); *B01J 37/0036* (2013.01); *B01J 37/0201* (2013.01); *B01J 37/031* (2013.01); *B01J 37/18* (2013.01); *C07C 29/156* (2013.01)

(56) References Cited

U.S. PATENT DOCUMENTS

| | | | |
|---|---|---|---|
| 4,777,313 | A | 10/1988 | Sofranko et al. |
| 9,833,774 | B2 | 12/2017 | Santos Castro et al. |
| 2005/0059839 | A1 | 5/2005 | Liu et al. |
| 2007/0297973 | A1 | 12/2007 | Chen |
| 2011/0006271 | A1* | 1/2011 | Bouchard ............... C03C 17/25 252/519.52 |
| 2016/0280606 | A1* | 9/2016 | O'Brien ............... C04B 35/6264 |

OTHER PUBLICATIONS

Search Report and Written Opinion for PCT/IB2018/060288 dated Jul. 8, 2019.

Onyestayak, et al., "Reac Kinet Meeh Cat, 121", 2017, 109-119.

Tahir, et al., "Performance analysis of nanostructured Ni0-In 2 0 3/Tio 2 catalyst for CO 2 photoreduction with H2 in a monolith photoreactor", Chemical Engineering Journal, vol. 285,, Oct. 17, 2015, 636-649.

Vinothkumar, et al., "Hydrogen production from water-methanol solution over visible light active indium-titanium oxide photocatalysts modified with copper oxide", International Journal of Hydrogen Energy, Elsevier Science Publishers B.V. Barking, GB, vol. 39, No. 22, Jun. 14, 2014, 11494-11500.

Wang, et al., "Recent advances in catalytic hydrogenation of carbon dioxide", Chem. Soc. Rev., 40, 3703-3727, Jul. 2011.

* cited by examiner

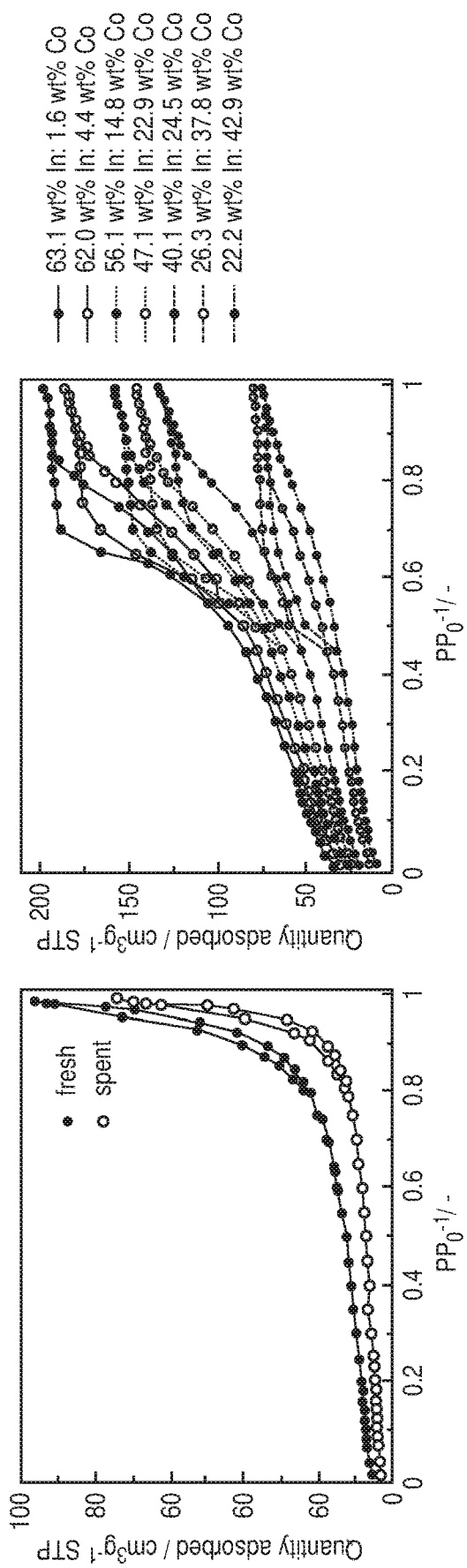
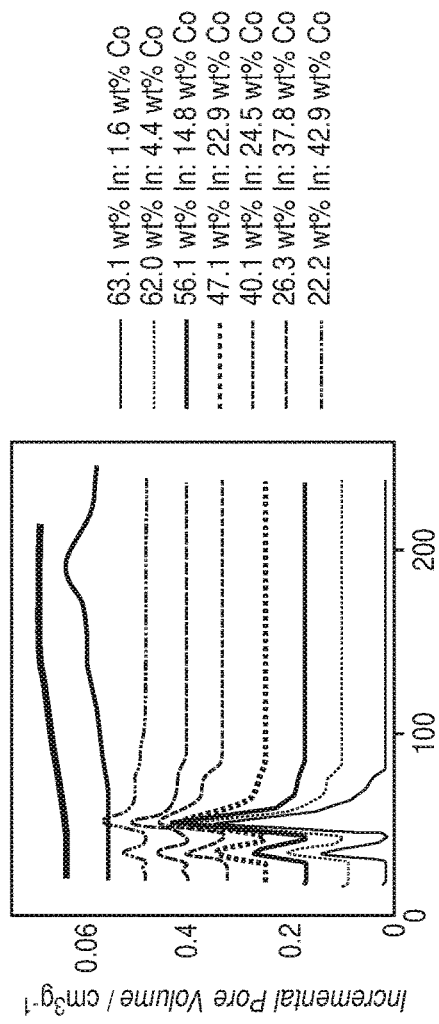
FIG. 14A
FIG. 14B
FIG. 14C

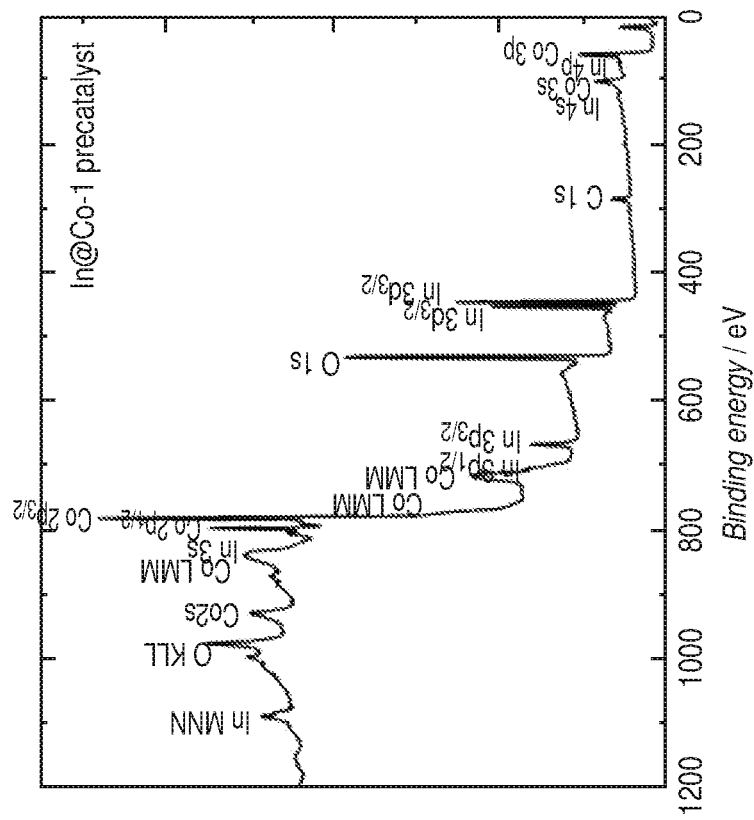
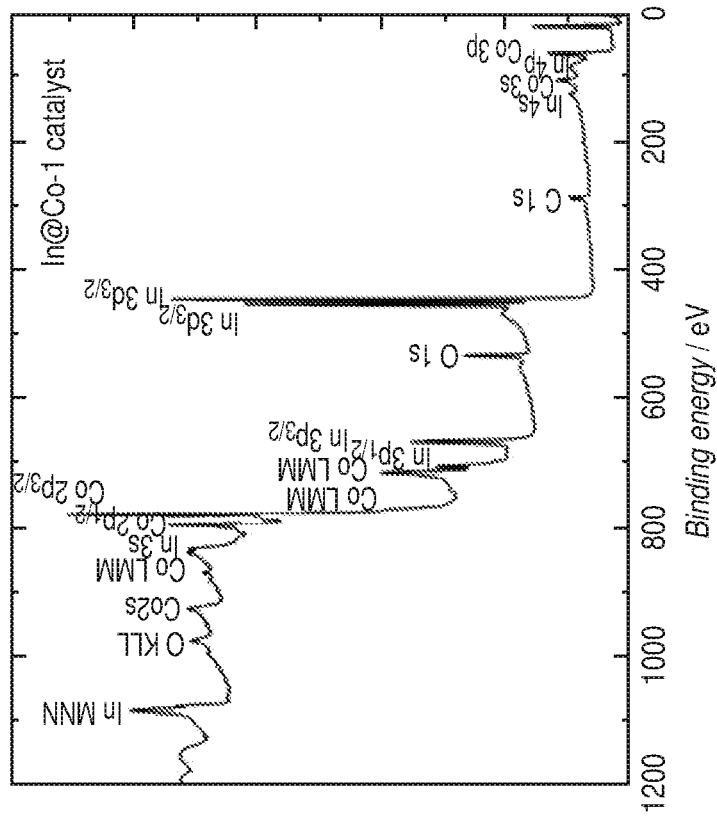

US 11,278,872 B2

INDIUM-BASED CATALYSTS AND PRE-CATALYSTS

BACKGROUND

Carbon dioxide hydrogenation into a valuable feedstock carries a two-fold positive effect: i) reducing the amount of $CO_2$ emitted to the atmosphere and ii) producing fine chemicals from an abundantly available C1 building block. Methanol is a chemical that is currently of high importance and demand. Traditionally, methanol is synthesized using a benchmark Cu—ZnO—$Al_2O_3$ catalyst and $CO_2$, CO and $H_2$ mixtures. When the same catalyst is applied to directly hydrogenate $CO_2$, severe deactivation and low selectivity to methanol are achieved.

SUMMARY

In general, embodiments of the present disclosure describe pre-catalysts and catalysts, methods of making the pre-catalysts and catalysts, methods of using the catalysts, and the like.

Accordingly, embodiments of the present disclosure describe a pre-catalyst comprising including one or more of indium oxide, indium hydroxide, indium oxyhydroxide, an active oxide, and a refractory oxide. In an embodiment, the pre-catalyst may comprise one or more of indium oxide, indium hydroxide, and indium oxyhydroxide mixed with one or more of an active oxide and a refractory oxide.

Embodiments of the present disclosure describe a pre-catalyst comprising a support including one or more of an active oxide and a refractory oxide, and one or more of indium oxide, indium hydroxide, and indium oxyhydroxide on a surface of the support.

Embodiments of the present disclosure describe a method of making a pre-catalyst comprising contacting an indium precursor solution and a carrier including an active oxide; heating at a first select temperature to remove a suitable amount of solvent; and calcining at a second select temperature to form a pre-catalyst, wherein the pre-catalyst includes one or more of indium oxide, indium hydroxide, and indium oxyhydroxide mixed with the active oxide.

Embodiments of the present disclosure describe a method of making a pre-catalyst comprising contacting an indium salt and one or more of an active oxide and a refractory oxide in a ball mill sufficient to form the pre-catalyst, wherein the pre-catalyst includes one or more of indium oxide, indium hydroxide, and indium oxyhydroxide mixed with one or more of the active oxide and the refractory oxide.

Embodiments of the present disclosure describe a method of making a pre-catalyst comprising contacting a precursor solution with a solvent, wherein the precursor solution includes an indium precursor and a second precursor; and heating at a select temperature and pH to form the pre-catalyst, wherein the pre-catalyst includes one or more of indium oxide, indium hydroxide, and indium oxyhydroxide mixed with an active oxide nanoparticle.

Embodiments of the present disclosure describe a method of making a pre-catalyst comprising contacting an active metal-based MOF with one or more of a silica source and an indium precursor solution; thermally decomposing the MOF at a first temperature; and calcining at a second temperature to form the pre-catalyst, wherein the pre-catalyst includes one or more of indium oxide, indium hydroxide, and indium oxyhydroxide mixed with an active oxide nanoparticle. A source of carbon (i.e. carbonate) may also be present in the pre-catalyst. In an embodiment, the method may comprise contacting indium precursor with pyrolysed cobalt-based Metal Organic Framework (MOFs) or MOF/silica or MOF/zirconia or MOF/alumina composite; calcining at an elevated temperature to form indium oxide supported on a cobalt oxide nanoparticle.

Embodiments of the present disclosure describe how the pre-catalysts of the present disclosure may be treated in a reducing atmosphere ($H_2/CO_2$ mixture, alkane, alkene, diluted $H_2$ in Ar, $N_2$, CO) at elevated temperature ranging from 150-400° C. in order to prepare the catalysts. The reducing atmosphere may be provided during or prior to reaction. In a preferred embodiment, this reductive treatment is done in the presence of a carbon source (e.g., CO2, hydrocarbons, carbon, etc.) either in the treatment gas or carbon is present in the composition of the pre-catalyst.

Embodiments of the present disclosure describe methods of forming a catalyst comprising subjecting a pre-catalyst to a reductive treatment under reaction conditions or prior to a reaction, wherein the pre-catalyst includes one or more of indium oxide, indium hydroxide, and indium oxyhydroxide mixed with an active oxide nanoparticle.

Embodiments of the present disclosure describe a method of synthesizing methanol and/or olefins comprising flowing a fluid composition including at least carbon dioxide and hydrogen over a pre-catalyst to activate the pre-catalyst and produce one or more of methanol and olefins, wherein the pre-catalyst includes one or more of indium oxide, indium hydroxide, and indium oxyhydroxide mixed with an active oxide nanoparticle, with or without a refractory oxide; and recovering methanol.

The details of one or more examples are set forth in the description below. Other features, objects, and advantages will be apparent from the description and from the claims.

BRIEF DESCRIPTION OF DRAWINGS

This written disclosure describes illustrative embodiments that are non-limiting and non-exhaustive. In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

Reference is made to illustrative embodiments that are depicted in the figures, in which:

FIGS. 14A-14C is a graphical view of nitrogen adsorption isotherms of a) fresh and spent In@Co-1; b) catalysts from In@Co-2 series; c) Pore size distribution of Co@ In-1 and Co@In-2 series of the catalyst, according to one or more embodiments of the present disclosure.

FIGS. 20A-20B shows X-ray photoelectron spectroscopy survey analysis of the In@Co-1 solid before and after reaction, according to one or more embodiments of the present disclosure.

DETAILED DESCRIPTION

Figure 1:
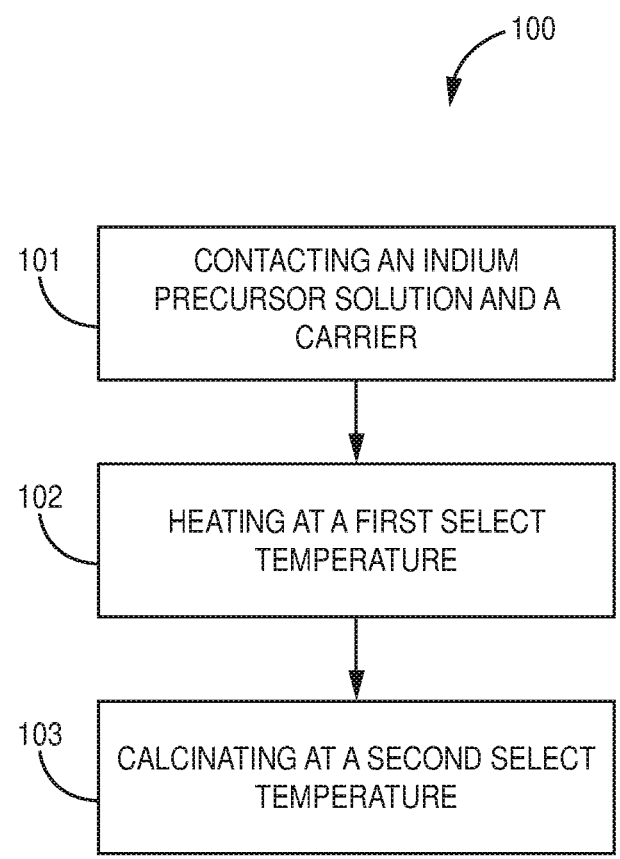
FIG. 1 is a flowchart of a method of making a catalyst of the present disclosure by wet impregnation, according to one or more embodiments of the present disclosure.

The invention of the present disclosure relates to catalysts and pre-catalysts, methods of making catalysts and pre-catalysts, and methods of using catalysts in the synthesis of various chemical species including, but not limited to, one or more of methanol and olefins. The catalysts may be obtained from the pre-catalysts described herein. The pre-catalysts may include one or more of indium oxide, indium hydroxide, indium oxyhydroxide, an active oxide, and a refractory oxide. The pre-catalysts may be activated by a reductive treatment. The reductive treatment may proceed during reaction (e.g., under reaction conditions) and/or prior to reaction via a reductive pre-treatment. During activation, one or more of indium oxide, indium hydroxide, and indium oxyhydroxide may be reduced to indium, providing an activated catalyst including indium and an active oxide, such as a reducible oxide (e.g., cobalt oxide). The catalysts obtained from the pre-catalysts may be used in various reactions, such as $CO_2$ hydrogenation to produce methanol and/or olefins.

The pre-catalysts of the present disclosure may be fabricated via any of a variety of methods, including, but not limited to, one or more of impregnation, precipitation or co-precipitation, ball milling, and metal-organic framework (MOF)-mediated synthesis, among other methods. The pre-catalysts fabricated according to the methods of the present disclosure may be activated, via a reductive treatment (with or without the presence of a carbon source), into the catalysts of the present disclosure. Catalysts obtained from the pre-catalysts described herein may exhibit structural and performance characteristics, among other properties, that are far superior to conventional catalysts. For example, the catalysts of the present disclosure may be superior to conventional catalysts at least in terms of indium loading, yield, selectivity, and activity, without any deactivation for at least about 50 h of use.

While not wishing to be bound to a theory, the indium-based catalysts or pre-catalysts described herein may include supports containing active oxides (e.g., reducible oxides) and/or may include active oxides as the support. In an embodiment, the supports may include a reducible oxide that may, after activation, enhance interactions between indium and the reducible oxide. The enhanced interactions may enhance catalyst performance (e.g., yield, selectivity, activity, stability, etc.). For example, in an embodiment, indium and a reducible oxide support may interact synergistically to activate one or more of $CO_2$ and $H_2$ for $CO_2$ hydrogenation, while also stabilizing the product (e.g., methanol and/or olefins). In another example, indium addition may tune the reactivity of a methanation catalyst by preventing the hydrogenolysis step of C—O bond from occurring upon formation of $CH_2$—O*.

The enhanced interactions may also permit catalysts with higher indium loadings relative to conventional catalysts. An indium content of the catalyst may range from about 1% by weight to about 50% by weight. In many embodiments, an indium content of the catalyst may range from about 5% by weight to about 25% by weight. In a preferred embodiment, an indium content of the catalyst may be about 9% by weight. In a more preferred embodiment, an indium content may be about 20% by weight. In other embodiments, an indium content of the catalyst may be less than about 1% by weight or greater than about 50% by weight.

While not wishing to be bound by a theory, one explanation for the enhanced interactions between indium and, for example, a reducible oxide support may relate to the use or incorporation of mixed valence elements, compounds, materials, etc. While conventional catalysts are not based on mixed valence materials, in an embodiment, the catalysts of the present disclosure may use and/or incorporate cobalt oxide as a reducible oxide support. In many embodiments, cobalt oxide is present as a mixed valence cobalt oxide. For example, in an embodiment, the cobalt oxide support may include at least two cobalt states with different properties. One cobalt may be paramagnetic and one cobalt may be diamagnetic, providing at least 1 extra electron. Since all indium phases are generally inactive alone or by themselves, the addition of a reducible or mixed valence cobalt oxide may be used to activate indium, which in turn may activate, for example, hydrogen and carbon dioxide and make them react to form a desired product (e.g., methanol). In this way, the reducible oxide may act as a support and as a promoter, unlike any other conventional indium-based catalysts.

Definitions

The terms recited below have been defined as described below. All other terms and phrases in this disclosure shall be construed according to their ordinary meaning as understood by one of skill in the art.

As used herein, "active oxide" refers to any oxide that is active in reactions of the present disclosure. For example, an active oxide may refer to an oxide that is active in $CO_2$ hydrogenation. Active oxides may include reducible oxides, among other chemical species.

As used herein, "reducible oxide" refers to any element, compound, and/or material capable of being reduced in a reaction. For example, a reducible oxide may refer to any oxide including at least one metal that may be reduced by a reductive treatment. The metals may include, but are not limited to, one or more of cobalt, nickel, copper, manganese, iron, and vanadium.

As used herein, "mixed valence oxide" refers to any element, compound, and/or material present in more than one oxidation state. For example, a mixed valence oxide may include any compound and/or material containing an element that is present in more than one oxidation state.

As used herein, "bulk catalyst" refers to a catalyst without a support. For example, a bulk catalyst may include an unsupported catalyst.

As used herein, "supported catalyst" refers to a catalyst with a support.

As used herein, "pre-catalyst" refers to pre-catalysts made according to the methods of the present disclosure. For example, pre-catalyst may refer to pre-catalysts that include one or more of indium oxide, indium hydroxide, and indium oxyhydroxide, mixed with one or more active oxides (e.g., one or more reducible oxides), either with or without the presence of refractory oxides.

As used herein, "catalyst" refers to any material active in a reaction. For example, catalyst may refer to a catalyst active in $CO_2$ hydrogenation that is obtained from the pre-catalysts described herein. In many embodiments, the pre-catalysts may be activated into the catalysts by a reductive treatment as described herein.

As used herein, "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo. Accordingly, adding, stirring, treating, tumbling, vibrating, shaking, mixing, and applying are forms of contacting to bring two or more components together.

As used herein, "calcinating" refers to heating to a high temperature.

As used herein, "heating" refers to increasing a temperature. For example, heating may refer to exposing or subjecting any object, material, etc. to a temperature that is greater than a current or previous temperature. Heating may also refer to increasing a temperature of any object, material, etc. to a temperature that is greater than a current or previous temperature of the object, material, etc.

As used herein, "flowing" refers to contacting, feeding, flowing, passing, injecting, introducing, and/or providing the fluid composition (e.g., a feed gas).

As used herein, "recovering" refers to obtaining any product resulting from a reaction. The product may include the product and one or more other chemical species. The product may also be an isolated product without any impurities, with a low concentration of impurities, or with a negligible concentration of impurities.

Embodiments of the present disclosure describe catalysts obtained from the pre-catalysts described herein. The catalysts of the present disclosure may be a supported catalyst or a bulk catalyst. A supported catalyst generally refers to a catalyst with a support. A bulk catalyst generally refers to a catalyst without a support. In many embodiments, the catalyst is a supported catalyst. In other embodiments, the catalyst is a bulk catalyst. The catalyst may take any form. For example, in an embodiment, a form of the catalyst may include one or more of extrudates, granules, spheres, monoliths, particles, pellets, beads, films, and layers.

The pre-catalysts from which the catalysts may be obtained may include one or more of indium oxide, indium hydroxide, indium oxyhydroxide, an active oxide, and a refractory oxide. In many embodiments, the pre-catalyst may be present as a mixture of one or more of indium oxide, indium hydroxide, indium oxyhydroxide, an active oxide, and a refractory oxide. For example, in many embodiments, the catalysts may be obtained from a mixture of one or more of indium oxide, indium hydroxide, indium oxyhydroxide, an active oxide, and a refractory oxide. In some embodiments, the active oxide is a reducible oxide. In these embodiments, the catalysts may be obtained from a mixture of one or more of indium oxide, indium hydroxide, indium oxyhydroxide, a reducible oxide, and a refractory oxide.

The catalysts obtained from the pre-catalysts described herein may be active in $CO_2$ hydrogenation. To form the catalysts, the pre-catalysts may be subjected to a reductive treatment. That is, the pre-catalysts may be activated under reaction conditions suitable for, or related to, $CO_2$ hydrogenation. For example, in an embodiment, the catalysts may be formed from pre-catalysts activated during $CO_2$ hydrogenation or under reaction conditions related to $CO_2$ hydrogenation, without any pretreatment or prior activation. In the alternative, the pre-catalysts may be activated prior to $CO_2$ hydrogenation. For example, in an embodiment, the pre-catalysts may be activated via pre-treatment in a reducing atmosphere at elevated temperature(s). The reducing atmosphere may include one or more of $H_2/CO_2$ mixture, alkane, alkene, and diluted $H_2$ in one or more of Ar, $N_2$, and CO. The elevated temperature may range from about 150° C. to about 400° C. The pre-catalysts upon activation or the catalysts may include at least about 10% of metal species in oxidic matrix. In some embodiments, the metal species are present in an amount that is less than 10% or more than 10%.

As described herein, the catalysts obtained from the pre-catalysts of the present disclosure may be used for the synthesis of methanol and olefins, among other chemical species. For example, in an embodiment, gas streams containing carbon dioxide may be fed to the catalyst to produce methanol or olefins. In an embodiment, a carbon dioxide-containing gas stream is a carbon dioxide-rich syngas. The carbon dioxide-containing gas stream may include one or more of carbon dioxide, hydrogen, carbon monoxide, and methane, among other chemical species. In many embodiments, the catalyst is a hydrogenation catalyst or a carbon dioxide hydrogenation catalyst for the production of methanol. For example, in an embodiment, the catalyst is used in the hydrogenation of carbon dioxide to produce methanol. In other embodiments, the catalyst may be combined with other catalysts for the production of olefins.

Embodiments of the present disclosure describe pre-catalysts from which the catalysts may be obtained. The pre-catalysts may comprise one or more of indium oxide, indium hydroxide, indium oxyhydroxide, an active oxide, and a refractory oxide. In some embodiments, the pre-catalysts may be present as a mixture of one or more of indium oxide, indium hydroxide, indium oxyhydroxide, an active oxide, and a refractory oxide. In other embodiments, the pre-catalysts may further comprise a zeolite and/or zirconia (e.g., zirconia beads).

The pre-catalysts may be a bulk pre-catalyst or a supported pre-catalyst. A supported pre-catalyst may comprise a support and one or more of indium oxide, indium hydroxide, and indium oxyhydroxide on a surface of the support. The support may be characterized by a high surface area and a high porosity, and may be highly stable. For example, in an embodiment, the support is a solid support. In an embodiment, the support is a porous solid support. In an embodiment, the support is a carrier. In an embodiment, the support is a porous carrier. In an embodiment, the support is a particle. In an embodiment, the support is a nanoparticle.

The support may include any material capable of supporting one or more of indium oxide, indium hydroxide, and indium oxyhydroxide. In many embodiments, the support may include an active oxide. An active oxide may include any oxide that is active in $CO_2$ hydrogenation (e.g., active in the synthesis of methanol and/or olefins via $CO_2$ hydrogenation). In some embodiments, the active oxide may include a reducible oxide. In these embodiments, the support may include a reducible oxide and/or one or more other active oxides. In other embodiments, the support may further comprise a refractory oxide. In this way, one or more of indium oxide, indium hydroxide, and indium oxyhydroxide may be mixed with or supported on one or more of an active oxide (e.g., a reducible oxide) and a refractory oxide.

A bulk pre-catalyst may comprise one or more of indium oxide, indium hydroxide, indium oxyhydroxide, an active oxide, and a refractory oxide. In many embodiments, the one or more of indium oxide, indium hydroxide, and indium oxyhydroxide may be mixed with one or more of the active oxide and the refractory oxide. For example, in an embodiment, the bulk pre-catalyst may comprise one or more of indium oxide, indium hydroxide, and indium oxyhydroxide mixed with an active oxide (e.g., a reducible oxide). In an embodiment, the bulk pre-catalyst may comprise one or more of indium oxide, indium hydroxide, and indium oxyhydroxide mixed with an active oxide and a refractory oxide.

Indium oxide may be characterized by the formula $In_2O_3$ and variations thereof. In a preferred embodiment, indium oxide is $In_2O_3$.

An active oxide may include any oxide that is active in $CO_2$ hydrogenation. In many embodiments, the active oxide may include a reducible oxide. A reducible oxide may include any oxide that is capable of being reduced. For example, in an embodiment, a reducible oxide is any oxide including at least one metal that may be reduced via a pre-treatment and/or under reaction conditions related to or suitable for producing a desired product (e.g., methanol). The at least one metal may include one or more of cobalt, nickel, copper, manganese, iron, and vanadium. The reducible oxide may include a mixed valence oxide. For example, a mixed valence oxide may include any oxide containing an element present in more than one oxidation state. In an embodiment, the reducible oxide includes cobalt oxide. In a preferred embodiment, the reducible oxide includes a mixed valence cobalt oxide. A suitable cobalt oxide or mixed valence cobalt oxide may be characterized by the formula $Co_3O_4$, or cobalt (II,III) oxide.

A refractory oxide may include any oxide that is non-reducible or substantially non-reducible. In some embodiments, a refractory oxide is mixed with an active oxide. The non-reducible oxide may include one or more of zirconium dioxide ($ZrO_2$), silica ($SiO_2$), alumina ($Al_2O_3$), gallium oxide ($Ga_2O_3$), cerium oxide ($CeO_2$), vanadium oxide ($V_2O_5$), chromium oxide ($Cr_2O_3$), titanium dioxide ($TiO_2$), magnesium oxide (MgO), zinc oxide (ZnO), tin oxide ($SnO_2$), and carbon black (C). In an embodiment, the refractory oxide is zirconium dioxide ($ZrO_2$). In an embodiment, zirconium dioxide is mixed with a reducible oxide, such as a mixed valence cobalt oxide.

In some embodiments, the catalyst may further comprise one or more of lubricants, peptizers, plasticizers, porogens, binders, and fillers.

In an embodiment, the pre-catalyst comprises one or more of indium oxide, indium hydroxide, and indium oxyhydroxide mixed with or supported on one or more of an active oxide (e.g., reducible oxide), refractory oxide, zeolite, and carbon.

In an embodiment, the pre-catalyst comprises a support including an active oxide and one or more of indium oxide, indium hydroxide, and indium oxyhydroxide on a surface of the support. In an embodiment, the pre-catalyst comprises a support including a reducible oxide and one or more of indium oxide, indium hydroxide, and indium oxyhydroxide on a surface of the support. In any of these embodiments, the pre-catalyst may further comprise one or more of active oxides, refractory oxides, and zeolite.

In an embodiment, the pre-catalyst comprises a support including cobalt oxide, and indium oxide on a surface of the support. In an embodiment, the pre-catalyst comprises a support including a mixed valence cobalt oxide, and indium oxide on a surface of the support. In an embodiment, the pre-catalyst comprises a carrier including cobalt oxide, and indium oxide on a surface of the carrier. In an embodiment, the pre-catalyst comprises indium oxide supported on cobalt oxide. In an embodiment, the pre-catalyst comprises indium oxide supported on a mixed valence cobalt oxide.

In an embodiment, the pre-catalyst comprises indium oxide supported on a cobalt oxide nanoparticle. In an embodiment, the pre-catalyst comprises indium oxide supported on a mixed valence cobalt oxide nanoparticle. An average diameter of the nanoparticles may be less than about 1 µm. In an embodiment, an average diameter of the nanoparticles may be less than about 0.9 µm, less than about 0.8 µm, less than about 0.7 mm, less than about 0.6 µm, less than about 0.5 µm, less than about 0.4 µm, less than about 0.3 µm, less than about 0.2 µm, or less than about 0.1 µm. In a preferred embodiment, an average diameter of the nanoparticles is about 0.06 µm.

In an embodiment, the pre-catalyst comprises indium oxide supported on a cobalt-based metal-organic framework including one or more of silica and carbon.

In an embodiment, the pre-catalyst comprises indium oxide supported on a mixture of cobalt oxide and a refractory oxide. In an embodiment, the pre-catalyst comprises indium oxide supported on a mixture of a mixed valence cobalt oxide and a refractory oxide. In an embodiment, the pre-catalyst comprises indium oxide supported on a mixture of cobalt oxide and zirconia beads. In an embodiment, the pre-catalyst comprises indium oxide supported on a mixture of a mixed valence cobalt oxide and zirconia beads.

Embodiments of the present disclosure describe a variety of methods of making pre-catalysts. The methods may include, but are not limited to, one or more of impregnation (e.g., incipient wetness impregnation (IWI)), ball milling (e.g., dry ball milling), co-precipitation, and MOF-mediated synthesis. Each of the methods may be used to make pre-catalysts with different properties, features, and characteristics, as described in greater detail herein.

FIG. 1 is a flowchart of a method 100 of making a pre-catalyst of the present disclosure by impregnation (e.g., wet impregnation, incipient wetness impregnation (IWI), or dry impregnation), according to one or more embodiments of the present disclosure. The method 100 may comprise contacting 101 an indium precursor solution and a carrier including an active oxide, heating 102 at a first select temperature to remove a suitable amount of solvent, and calcining 103 at a second select temperature to form a pre-catalyst, wherein the pre-catalyst includes one or more of indium oxide, indium hydroxide, and indium oxyhydroxide mixed with the active oxide.

At step 101, a carrier and an indium precursor solution are contacted. Contacting may include adding a volume of precursor solution dropwise to the carrier sufficient to at least fill the pores of the porous carrier (e.g., impregnate the porous support with the precursor solution). Contacting may further or in the alternative include mixing by physical methods (e.g., shaking, vibrating, etc.). In many embodiments, the indium precursor solution is added dropwise to the carrier. In other embodiments, any method of contacting known in the art may be used, including, but not limited to, pouring, adding, and immersing, among others.

The carrier may be porous or non-porous. In many embodiments, the carrier is a porous carrier. The carrier may include any of the active oxides described herein. In many embodiments, the carrier includes a reducible oxide. For example, in an embodiment, the carrier includes cobalt oxide. In a preferred embodiment, the carrier includes a mixed valence cobalt oxide, such as $Co_3O_4$ or cobalt (II,III) oxide. These shall not be limiting, as any of the supports and/or active oxides of the present disclosure may be used herein.

The indium precursor solution may include an indium salt and a solvent. In an embodiment, the indium salt is indium nitrate (e.g., $In(NO_3)_3$). In an embodiment, the indium salt is indium nitrate hydrate (e.g., $In(NO_3)_3 \cdot xH_2O$). In other embodiments, the indium salt may include one or more of indium sulfamate, indium chloride, indium bromide, indium sulfate, indium carbonate, indium acetate, indium formate, indium acetylacetonate, and indium iodide. The solvent may include one or more of water, organic solvents, and inorganic solvents. In many embodiments, the solvent is water, forming an aqueous indium precursor solution. The concentration of indium or the indium salt may be varied to achieve catalysts with different indium loadings. For example, a concentration of indium in the precursor solution may range from about 0.1M to about 1.5M.

A volume of the indium precursor solution added to the carrier may be any volume suitable to form a catalyst with one or more of indium oxide, indium hydroxide, and indium oxyhydroxide on a surface of the carrier. In many embodiments, a volume of the indium precursor solution added to the carrier is any volume suitable to at least fill the pores of a porous carrier. In many embodiments, the volume of the indium precursor solution added dropwise to the carrier is greater than or equal to the pore volume of the carrier. For example, the volume of precursor may range from about 0.1 mL per gram of support to about 20 mL per gram of support.

In an embodiment, the volume of indium precursor may range from about 0.1 to about 1 mL per gram of support (e.g., for wet incipient impregnation). In an embodiment, the volume of indium precursor may range from about 1 mL to about 20 mL per gram of support (e.g., wet impregnation). In these embodiments, the method 100 may proceed by wet impregnation or wet incipient impregnation. In other embodiments, the volume of the indium precursor solution added dropwise to the carrier is about equal to the pore volume of the carrier. In these embodiments, the method 100 may proceed by dry impregnation.

At step 102, the carrier is heated to remove (e.g., evaporate) a suitable amount of solvent. Heating may include heating to or at a temperature. For example, in an embodiment, heating includes exposing, subjecting, and/or applying a temperature that is greater than a current or previous temperature. A suitable amount of solvent may include any amount removed that is sufficient to deposit one or more of indium oxide, indium hydroxide, and indium oxyhydroxide on or within the carrier. In many embodiments, the indium oxide is deposited on a surface of the carrier. Heating may proceed at a temperature ranging from about 40° C. to about 70° C. In some embodiments, heating may proceed at a temperature of about 60° C. In other embodiments, heating may proceed at a temperature less than about 40° C. or greater than about 70° C.

In some embodiments, steps 101 and 102 may be repeated one or more times before proceeding to step 103. For example, in an embodiment, the contacting 101 and heating 102 steps are performed one time, two times, three times, or four or more times before proceeding to step 103. In a preferred embodiment, the contacting 101 and heating 102 steps are performed three times before proceeding to step 103. In this way, catalysts with higher indium loadings may be achieved.

At step 103, the carrier is calcined to form the pre-catalyst. Calcining may include heating to or at a high temperature. In some embodiments, calcining includes heating to or at a high temperature in air (e.g., static air) for a select period of time. The temperature may be at least about 400° C. For example, in some embodiments, the temperature may be about 400° C., about 450° C., about 500° C., about 550° C., about 600° C., about 650° C., about 700° C., about 750° C., about 800° C., about 850° C., about 900° C., about 950° C., about 1000° C., about 1050° C., about 1100° C., about 1150° C., or about 1200° C. In other embodiments, the temperature may be less than about 400° C. or greater than about 1200° C. The select period of time may include at least about 1 h. For example, in some embodiments, the select period of time is at least about 1 h, about 2 h, about 3 h, about 4 h, about 5 h, about 6 h, about 7 h, and greater than about 7 h. In other embodiments, the select period of time is less than about 1 h. In many embodiments, calcining proceeds at about 450° C. in a static air for about 7 h.

Figure 2:
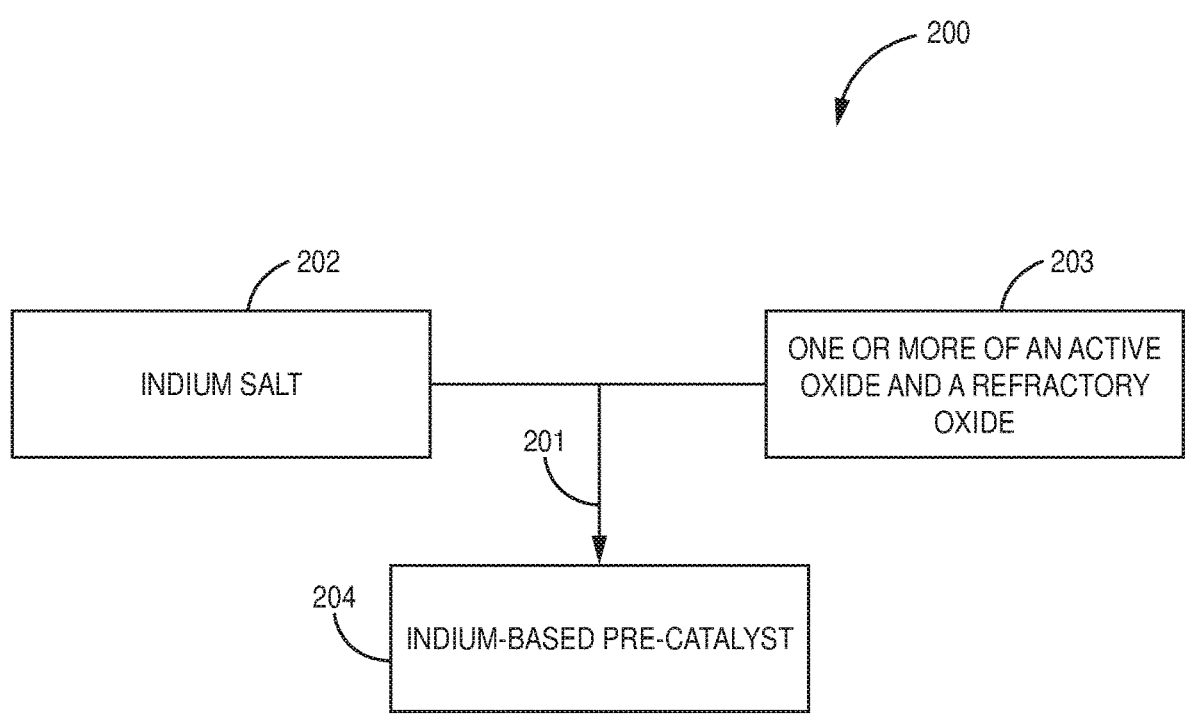
FIG. 2 is a flowchart of a method of making a catalyst of the present disclosure by ball milling, according to one or more embodiments of the present disclosure.

FIG. 2 is a flowchart of a method 200 of making a pre-catalyst of the present disclosure by ball milling, according to one or more embodiments of the present disclosure. The method may comprise contacting 201 an indium salt 202 and one or more of an active oxide and a refractory oxide 203 in a ball mill sufficient to form the pre-catalyst 204, wherein the pre-catalyst includes one or more of indium oxide, indium hydroxide, and indium oxyhydroxide mixed with one or more of the active oxide and refractory oxide.

At step 201, an indium salt and one or more of an active oxide and a refractory oxide are contacted in a ball mill to form the pre-catalyst. Contacting may proceed according to any of the embodiments described herein. In addition or in the alternative, contacting may include grinding. Ball milling generally refers to an impaction process that may include two interacting objects, where at least one of the objects is a ball. Dry milling generally refers to components (e.g., compounds, elements, particles, etc.) that have been milled in the presence of a non-liquid (e.g., a vacuum, a gas, or a combination thereof), whereas wet milling generally refers to components that have been milled in the presence of a liquid. In many embodiments, dry ball milling is used to form the pre-catalyst. In a preferred embodiment, a planetary mill is used to form the pre-catalyst. A planetary mill is an example of a ball mill capable of grinding materials to smaller sizes.

In embodiments in which dry ball milling is used, the contacting may proceed under various conditions. In a preferred embodiment, contacting proceeds at about 400 rpm, 12 h, reverse mode wherein the direction of orbital rotation is changed periodically (e.g., every half hour), room temperature (the temperature is not controlled, with about 1 g of the powder and about 10-30 g of zirconia beads.

Any of the indium salts, active oxides including reducible oxides, and refractory oxides of the present disclosure may be used herein. In a preferred embodiment, the indium salt is indium nitrate and the reducible oxide is a mixed valence cobalt oxide. In embodiments including a refractory oxide, the refractory oxide is zirconium dioxide. In an embodiment, a mass of indium nitrate is about 90 mg and a mass of cobalt oxide is about 1 g.

Figure 3:
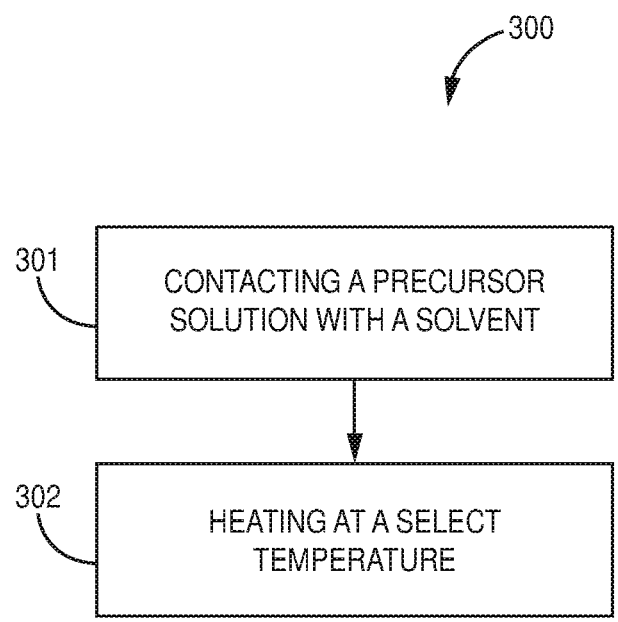
FIG. 3 is a flowchart of a method of making a catalyst of the present disclosure by co-precipitation, according to one or more embodiments of the present disclosure.

FIG. 3 is a flowchart of a method 300 of making a pre-catalyst of the present disclosure by co-precipitation, according to one or more embodiments of the present disclosure. The method may comprise contacting 301 a precursor solution with a solvent, wherein the precursor solution includes an indium precursor and a second precursor, and heating 302 at a select temperature and pH to form a pre-catalyst, wherein the pre-catalyst includes one or more of indium oxide, indium hydroxide, and indium oxyhydroxide mixed with (or on a surface of) an active oxide nanoparticle.

At step 301, a precursor solution is contacted with a solvent. Contacting may proceed according to any of the embodiments described herein. For example, in many embodiments, contacting includes adding the precursor solution dropwise to the solvent. In many embodiments, contacting is sufficient to co-precipitate the pre-catalyst from solution. In addition or in the alternative, contacting may include mixing or stirring.

The precursor solution includes an indium precursor and a second precursor. The indium precursor may include an indium salt. The indium salt may include any of the indium salts described herein. The second precursor may include a salt of one or more of cobalt, nickel, copper, manganese, iron, and vanadium. In many embodiments, the second precursor includes a cobalt salt. The cobalt salt may include one or more of cobalt sulfate, cobalt sulfonate, cobalt chloride, cobalt acetate, cobalt citrate, and cobalt lactate. In many embodiments, the cobalt salt is cobalt acetate. A solvent of the precursor solution may include any of the solvents described herein. In many embodiments, the solvent is water, forming an aqueous precursor solution. In an embodiment, the precursor solution includes about 0.1M of the indium precursor (e.g., indium acetate) and about 0.6M of the second precursor (e.g., cobalt acetate).

The solvent (i.e., the solvent with which the precursor solution is contacted) may include one or more of water, organic solvents, and inorganic solvents. For example, in an embodiment, the solvent may include one or more of ammonia hydroxide, water, and hydrogen peroxide. These shall not be limiting as any suitable solvent known in the art may be used herein.

At step 302, the solution is heated to form the pre-catalyst. Heating may include increasing to or at a temperature. In an embodiment, heating includes increasing to or at a temperature for a select period of time. In many embodiments, heating includes calcining sufficient to convert the precipitate into corresponding oxides. The temperature may be at least about 100° C. In a preferred embodiment, the temperature may be about 180° C. The select period of time may include at least about 1 h. For example, in some embodiments, the select period of time is at least about 1 h, about 2 h, about 3 h, about 4 h, about 5 h, about 6 h, about 7 h, and greater than about 7 h. In other embodiments, the select period of time is less than about 1 h. In a preferred embodiment, heating proceeds at about 180° C. for about 12 h.

Although not shown, in some embodiments, the method 300 may further include one or more of washing and/or drying of the precipitate or co-precipitated products, and/or separating residual solvent and impurities via centrifugation or filtration.

Figure 4:
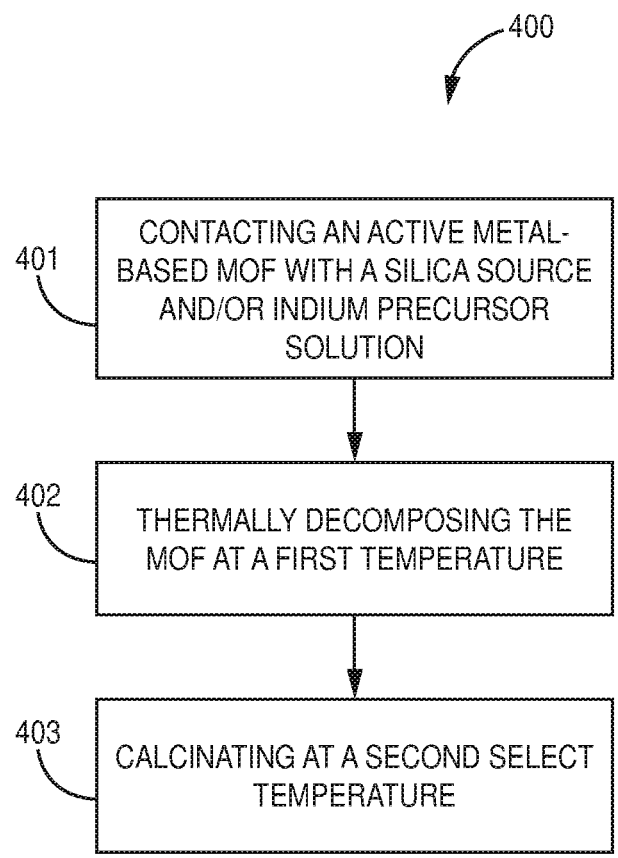
FIG. 4 is a flowchart of a method of making a catalyst of the present disclosure by MOF-mediated synthesis, according to one or more embodiments of the present disclosure.

FIG. 4 is a flowchart of a method 400 of making a catalyst of the present disclosure by metal-organic framework (MOF)-mediated synthesis, according to one or more embodiments of the present disclosure. The method 400 may comprise contacting 401 an active metal-based MOF with one or more of a silica source and an indium precursor solution; thermally decomposing 402 the MOF at a first temperature; and calcining 403 at a second temperature to form the pre-catalyst. In many embodiments, the pre-catalyst may include one or more of indium oxide, indium hydroxide, and indium oxyhydroxide mixed with an active oxide nanoparticle. A source of carbon (i.e., carbonate) may also be present in the pre-catalyst. In an embodiment, the method may comprise contacting indium precursor with pyrolysed cobalt-based Metal Organic Framework (MOFs) or MOF/silica or MOF/zirconia or MOF/alumina composite; calcining at an elevated temperature to form indium oxide supported on a cobalt oxide nanoparticle.

At step 401, an active metal-based MOF may be contacted with one or more of a silica source and an indium precursor solution. Contacting may proceed according to any of the embodiments of the present disclosure. For example, contacting may include adding dropwise, among other things.

The active metal-based MOF may be based on a single metal or mixed metals. The active metal of the MOF may include one or more of cobalt, nickel, copper, manganese, iron, and vanadium. For example, in many embodiments, the active metal-based MOF may include one or more of a cobalt-based MOF, a nickel-based MOF, a copper-based MOF, a manganese-based MOF, an iron-based MOF, a vanadium-based MOF, or a mixed metal MOF including one or more of the active metals. In a preferred embodiment, the active metal-based MOF is a cobalt-based MOF. The silica source may include any source of silica known in the art. In many embodiments, the silica source includes tetramethyl orthosilicate (TMOS). The indium precursor solution may include an indium salt and a solvent. Any of the indium salts and solvents of the present disclosure may be used herein. In many embodiments, the indium salt is indium nitrate and the solvent is water.

At step 402, the MOF is thermally decomposed at or to a first temperature. Thermally decomposing may generally refer to pyrolysis. The first temperature may range from about 400° C. to about 1000° C., or more preferably from about 400° C. to about 800° C. In a preferred embodiment, the first temperature is about 600° C. Thermally decomposing may proceed under inert gas flow. Inert gases may include one or more of nitrogen, helium, neon, argon, krypton, xenon, and radon. In some embodiments, the thermally decomposing step 402 may proceed without the removal of guest molecules (e.g., solvent or solvent molecules).

In general, any active metal-based or mixed active metal-based MOF may be thermally decomposed or undergo pyrolysis at the first temperature under inert gas flow. Accordingly, the contacting step 401 may proceed before or after the thermally decomposing step 402. For example, in an embodiment, the active metal-based MOF may be contacted with one or more of the silica source and the indium precursor solution prior to step 402. In an embodiment, the active metal-based MOF may be contacted with the silica source prior to step 402 and then the indium precursor solution may be contacted with the pyrolyzed active metal-based MOF. In an embodiment, the active metal-based MOF may be contacted with the silica source and the indium precursor solution prior to step 402. In an embodiment, the active metal-based MOF may be contacted separately with the silica source and the indium precursor solution prior to step 402.

At step 403, calcining proceeds at or to a second temperature to form the pre-catalyst. Calcining may proceed according to any of the embodiments of the present disclosure. For example, calcining may include heating to or at a high temperature. In a preferred embodiment, calcining proceeds at about 400° C.

In some embodiments, the method 400 may include performing the thermally decomposing (e.g., pyrolysis) step 402 and the calcining step 403 more than one time—for example, two or more times—to form the pre-catalyst.

The pre-catalyst may include one or more of indium oxide, indium hydroxide, and indium oxyhydroxide supported on or mixed with an active oxide nanoparticle (e.g., a cobalt oxide nanoparticle).

As described herein, all pre-catalysts may be activated into catalysts using the reaction conditions related to carbon dioxide hydrogenation (10-300 bar, 150-450° C., $H_2/CO_2$ ratio for about 6 h). An alternative is to activate the pre-catalyst prior to carbon dioxide hydrogenation by a separate pre-treatment in reducing atmosphere ($H_2/CO_2$ mixture, alkane, alkene, diluted $H_2$ in Ar, $N_2$, CO) at elevated temperature ranging from 150-400° C.

While not wishing to be bound to a theory, the ensemble of catalytic tests and ex-situ characterization of various activated Co—In catalysts conducted suggests either that $Co_3InC_{0.75}$ is the active phase, or that a bifunctional $In_2O_3/Co_3InC_{0.75}$ catalyst is involved. Chemical mappings of spent catalyst acquired with 1 nm lateral resolution by STEM-EELS depicted a quantitative reduction of both indium and cobalt in the form of nanoparticles (10 to 25 nm) which are all polycrystalline in nature.

Figure 5:
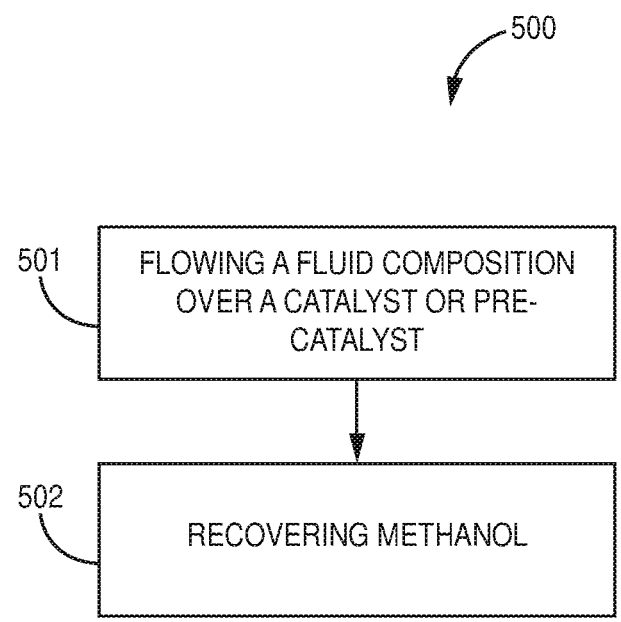
FIG. 5 is a flowchart of a method of producing or synthesizing methanol, according to one or more embodiments of the present disclosure.

FIG. 5 is a flowchart of a method 500 of producing or synthesizing methanol and/or olefins, according to one or more embodiments of the present disclosure. The method 500 may comprise flowing 501 a fluid composition including at least carbon dioxide and hydrogen over a pre-catalyst sufficient to produce one or more of methanol and olefins, wherein the pre-catalyst includes one or more of indium oxide, indium hydroxide, and indium oxyhydroxide mixed with one or more of an active oxide and a refractory oxide; and recovering 502 one or more of methanol and olefins.

The method 500 includes a pre-catalyst. In many embodiments, the pre-catalyst is subjected to a reductive treatment, either prior to or during the reaction. The reductive treatment may be with or without a presence of a carbon source. In a preferred embodiment, this reductive treatment may proceed in a presence of a carbon source ($CO_2$, hydrocarbons, carbon, etc.) either in the treatment gas or carbon is present in the composition of the pre-catalyst. In some embodiments, the pre-catalyst is activated under reaction conditions similar to or the same as those for $CO_2$ hydrogenation. In these embodiments, as shown in FIG. 5, the method includes a pre-catalyst. In the alternative, the method 500 may include a catalyst obtained from a pre-catalyst. For example, in some embodiments, the pre-catalyst may be activated via a reductive pre-treatment, which may occur prior to reaction. In these embodiments, the method includes a catalyst obtained from a pre-catalyst (not shown).

In some embodiments, the method may be used to produce or synthesize methanol via direct hydrogenation of carbon dioxide or indirect hydrogenation. In many embodiments, methanol is produced via direct hydrogenation of carbon dioxide. Any of the catalysts or pre-catalysts described herein may be used for method 500. In other embodiments, the method may be used to produce or synthesize olefins. In these embodiments, the catalyst or pre-catalyst may include one or more of indium oxide, indium hydroxide, indium oxyhydroxide, and an active oxide, and a refractory oxide.

At step 501, a fluid composition is flowed over a pre-catalyst sufficient to produce methanol. In embodiments in which the pre-catalyst is activated under reaction conditions, the flowing may activate the pre-catalyst and form the catalyst. In embodiments in which the pre-catalyst was subjected to a reductive pre-treatment, the flowing may produce methanol since the catalyst is already in an active state. Flowing may include contacting a fluid composition with a catalyst sufficient for one or more chemical species of the fluid composition to make physical contact with the catalyst, or sufficient to bring one or more chemical species of the fluid composition in immediate or close proximity to the catalyst. In this way, a reaction may proceed in a presence of the catalyst.

Flowing may proceed at various reaction conditions, including, but not limited to, one or more of temperature, pressure, and flow rate, among others. In many embodiments, flowing proceeds at reaction conditions sufficient for hydrogenation of carbon dioxide to proceed and form methanol. The reaction conditions may include one or more of a select temperature and a select pressure sufficient to one or more of reduce cobalt oxide and activate indium oxide for the hydrogenation of carbon dioxide and production of methanol. For example, flowing may proceed at a select temperature and/or select pressure. The select temperature may range from about 100° C. to about 400° C. In many embodiments, the select temperature is about 200° C. to about 300° C. In a preferred embodiment, the temperature is about 300° C. The select pressure may range from about 20 bar to about 400 bar. In many embodiments, the select pressure ranges from about 50 bar to about 80 bar. In a preferred embodiment, the select pressure is about 50 bar.

The fluid composition may include one or more chemical species in any phase, including, but not limited to, a gas phase, vapor phase, liquid phase, or solid phase. In many embodiments, the fluid composition includes one or more chemical species in a gas phase or vapor phase. In an embodiment, the fluid composition includes at least carbon dioxide and hydrogen. In an embodiment, the fluid composition includes carbon dioxide, hydrogen, and one or more other chemical species. The one or more other chemical species may include one or more of carbon monoxide, methane, and any other chemical species typically included in a carbon dioxide or carbon dioxide-rich gas stream. For example, in an embodiment, the fluid composition includes $CO_2$ or a $CO_2$-rich syngas including one or more of CO, $CO_2$, and $H_2$.

The fluid composition may include varying amounts of each chemical species. In an embodiment, the fluid composition is a mixture of about 30 to 60% carbon monoxide, 25 to 30% hydrogen, 5 to 15% carbon dioxide, and 0 to 5% methane. In an embodiment, a ratio of carbon dioxide to hydrogen ($CO_2$:$H_2$) ranges from about 1:1 to about 1:6

The pre-catalyst may include one or more of indium oxide, a reducible oxide (e.g., cobalt oxide), and a refractory oxide (e.g., non-reducible oxide). In many embodiments, the pre-catalyst includes indium oxide and a reducible oxide. For example, in a preferred embodiment, the pre-catalyst includes indium oxide supported on a mixed valence cobalt oxide. In other embodiments, the catalyst includes indium oxide on a support including a mixed valence cobalt oxide and one or more refractory oxides. For example, in an embodiment, the pre-catalyst includes indium oxide on a support including a mixed valence cobalt oxide and zirconium dioxide. These shall not be limiting as the pre-catalyst may include any of the catalysts of the present disclosure.

At step 502, one or more of methanol and olefins is recovered. Recovering may include obtaining methanol and/or olefins from the hydrogenation of carbon dioxide.

While not wishing to be bound by a theory, it is believed that the use of a reducible oxide, such as cobalt oxide, enhances interactions with indium oxide. For example, the cobalt oxide and indium oxide may perform synergistically in activating carbon dioxide and hydrogen, while also stabilizing the desired methanol product. In an embodiment, cobalt oxide is reduced at the reaction conditions and activates indium oxide. The activated indium oxide may activate carbon dioxide for hydrogenation and formation of the methanol product.

The following Examples are intended to illustrate the above invention and should not be construed as to narrow its scope. One skilled in the art will readily recognize that the Examiners suggest many other ways in which the invention could be practiced. It should be understand that numerous variations and modifications may be made while remaining within the scope of the invention.

Example 1

Fabrication of Pre-Catalyst Via Incipient Wetness Impregnation

An aqueous solution of $In(NO_3)_3 \cdot xH_2O$ of different concentrations was prepared and added dropwise into 1 g of a carrier ($Co_3O_4$) in three steps, each of 0.38 ml. The powders were mixed after every solution addition, shaken and heated at 60° C. during every step. IWI was followed by the calcination step at 450° C., static air for 7 h. Calcination was followed by a reduction treatment in $H_2/CO_2$ mixture (4:1) for 3 hours at 300° C. Varying the solution concentration, catalysts and pre-catalysts with different indium loadings were achieved.

Example 2

Fabrication of Pre-Catalyst Via Dry Ball Milling

Ball milled samples were prepared using planetary mill using 1 g of cobalt oxide and a known amount of $In(NO_3)_3$ under the following conditions: 400 rpm, reverse mode for 12 h, using 20 g of zirconia beads. Ball-milling was followed by a reduction treatment in $H_2/CO_2$ mixture (4:1) for 60 hours at 300° C. Varying the amount of added $In(NO_3)_3$, catalysts and pre-catalysts with different indium loadings were achieved.

Also, indium oxide supported on the mixture of $Co_3O_4$ and $ZrO_2$ was prepared in order to study the support effect.

Example 3

Fabrication of Pre-Catalyst Via Co-Precipitation

Figure 6:
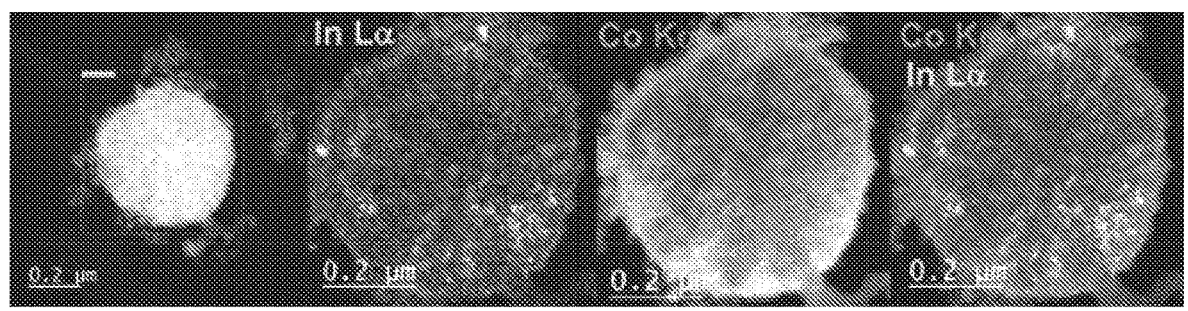
FIG. 6 is a TEM micrograph of catalysts fabricated via co-precipitation, according to one or more embodiments of the present disclosure.

Aqueous solution of indium and cobalt acetates were added dropwise using a syringe pump to the mixture of ammonia hydroxide, water and hydrogen peroxide under continuous stirring. After, the new solution was placed into an oven at 180° C. for 12 hours in an autoclave. Nanoparticles were obtained after washing and centrifugation, and drying. Drying was followed by a reduction treatment in $H_2/CO_2$ mixture (4:1) for 24 hours at 300° C. FIG. 6 is a TEM micrograph of catalysts fabricated via co-precipitation, according to one or more embodiments of the present disclosure.

Example 4

Fabrication of Pre-Catalyst Via MOF-Mediated Synthesis 0.8 g of MOF ZIF-8 is brought in contact with 5 ml of tetramethyl orthosilicate (TMOS) in an autoclave at 60° C. The powdered is filtered and TMOS is allowed to undergo hydrolysis within ZIF-8 pores at 50° C. for 30 h under nitrogen gas flow. The powder was dried at 60° C. afterwards. 0.4 g of indium nitrate was dissolved in 2 ml of water and the solution was added dropwise to ZIF-8 @ silica composite. Subsequently, the material underwent pyrolysis at 600° C. for 4 hours with 1° C. $min^{-1}$ temperature ramp. Calcination at 400° C. for 2 hours with the same temperature ramp was a concluding step.

Example 6

Synthesis of Methanol Using Indium Oxide Cobalt Oxide Catalyst

Figure 7:
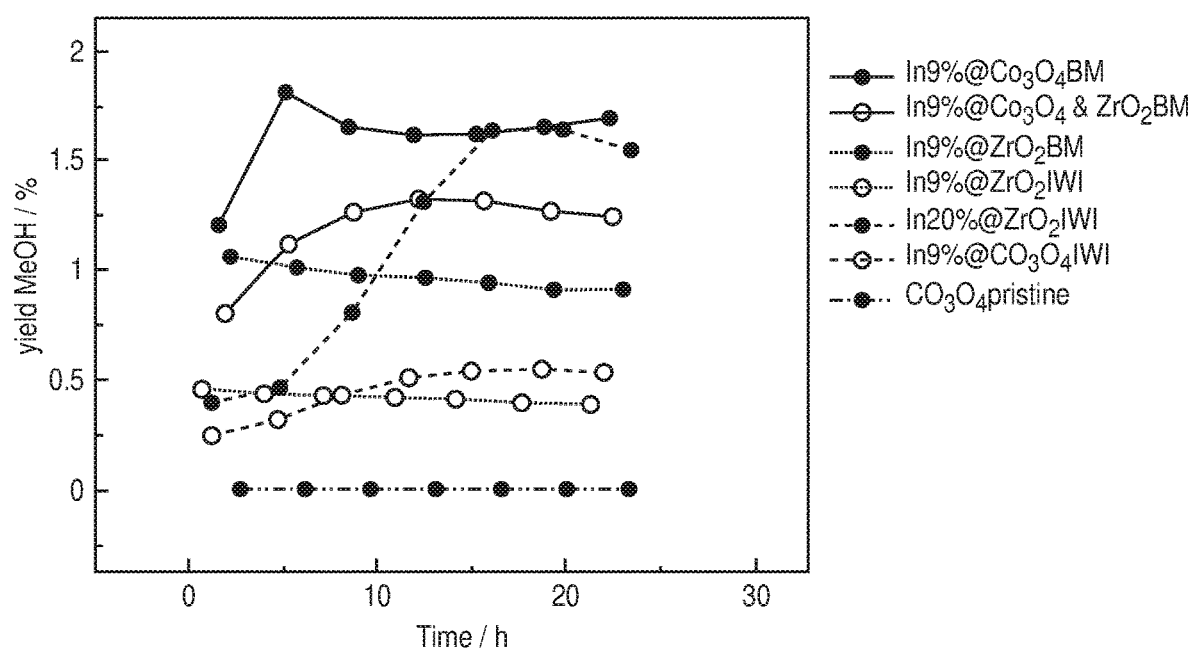
FIG. 7 is a graphical view of methanol yield from catalysts including indium oxide on different supports (conditions: 50 mg of catalyst, 50 bar of $CO_2:H_2$ (1:4) mixture, 300° C., WHSV 2 h$^{-1}$, and flow of 12 mL·min$^{-1}$), according to one or more embodiments of the present disclosure.

FIG. 7 is a graphical view of methanol yield from catalysts including indium oxide on different supports (conditions: 50 mg of catalyst, 50 bar of $CO_2:H_2$ (1:4) mixture, 300° C., WHSV 2 $h^{-1}$, and flow of 12 $mL \cdot min^{-1}$), according to one or more embodiments of the present disclosure.

Figure 8:
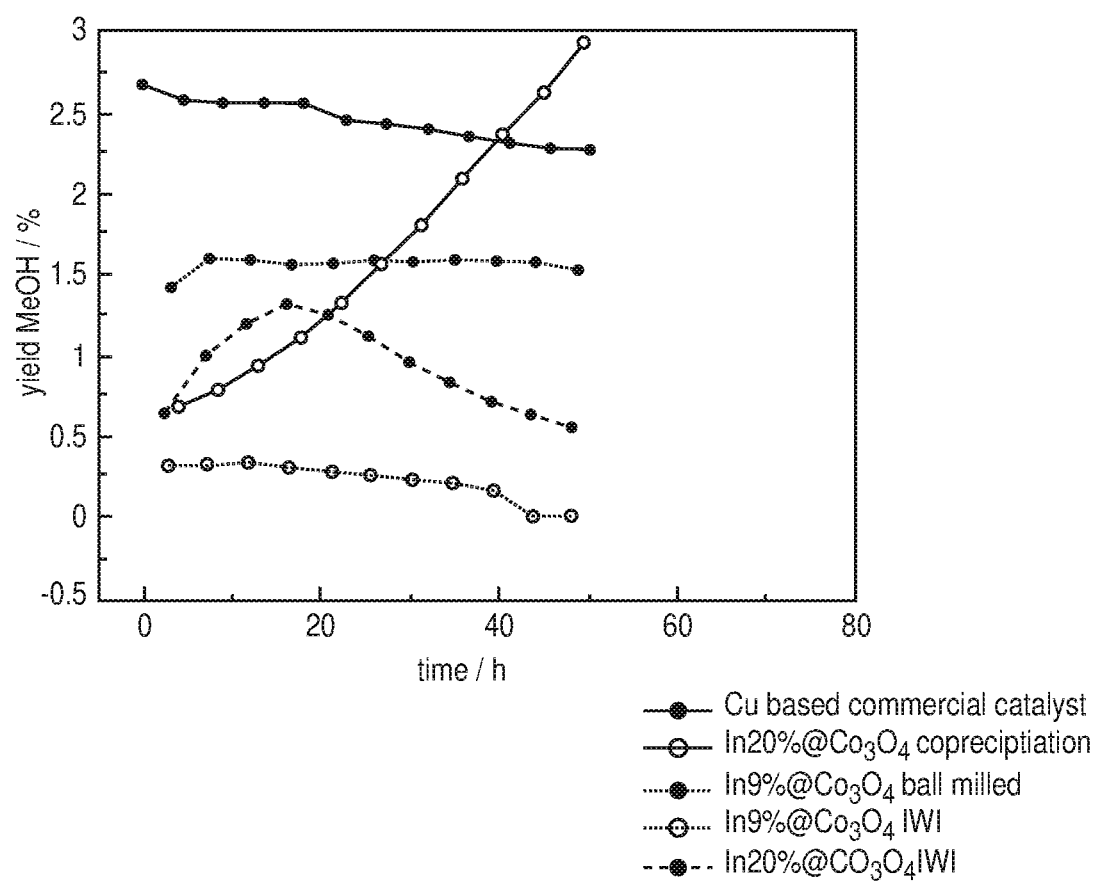
FIG. 8 is a graphical view of methanol yield from catalysts prepared by different methods (conditions: 50 mg of catalyst, 50 bar of $CO_2:H_2$ (1:4) mixture, 300° C., WHSV 2 h$^{-1}$, and flow of 12 mL·min$^{-1}$), according to one or more embodiments of the present disclosure.

FIG. 8 is a graphical view of methanol yield from catalysts prepared by different methods (conditions: 50 mg of catalyst, 50 bar of $CO_2:H_2$ (1:4) mixture, 300° C., WHSV 2 $h^{-1}$, and flow of 12 $mL \cdot min^{-1}$), according to one or more embodiments of the present disclosure.

Figure 9:
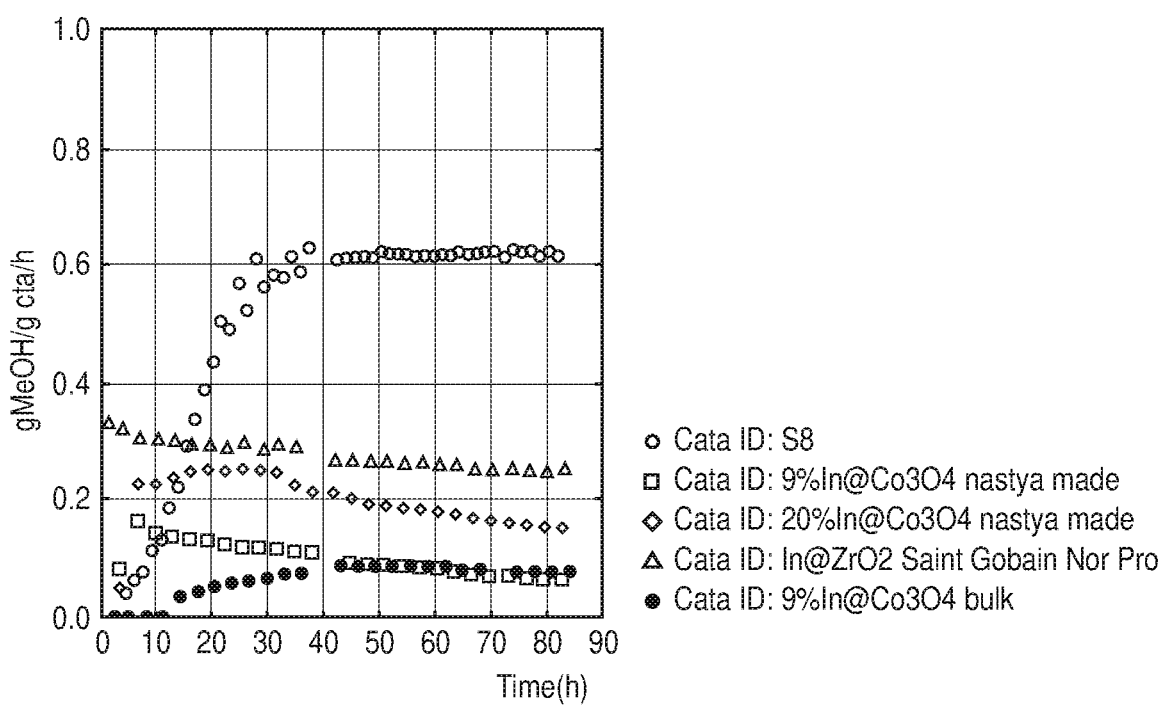
FIG. 9 is a graphical view of methanol yield for various catalysts, according to one or more embodiments of the present disclosure.

FIG. 9 is a graphical view of methanol yield for various catalysts, according to one or more embodiments of the present disclosure.

Figure 10:
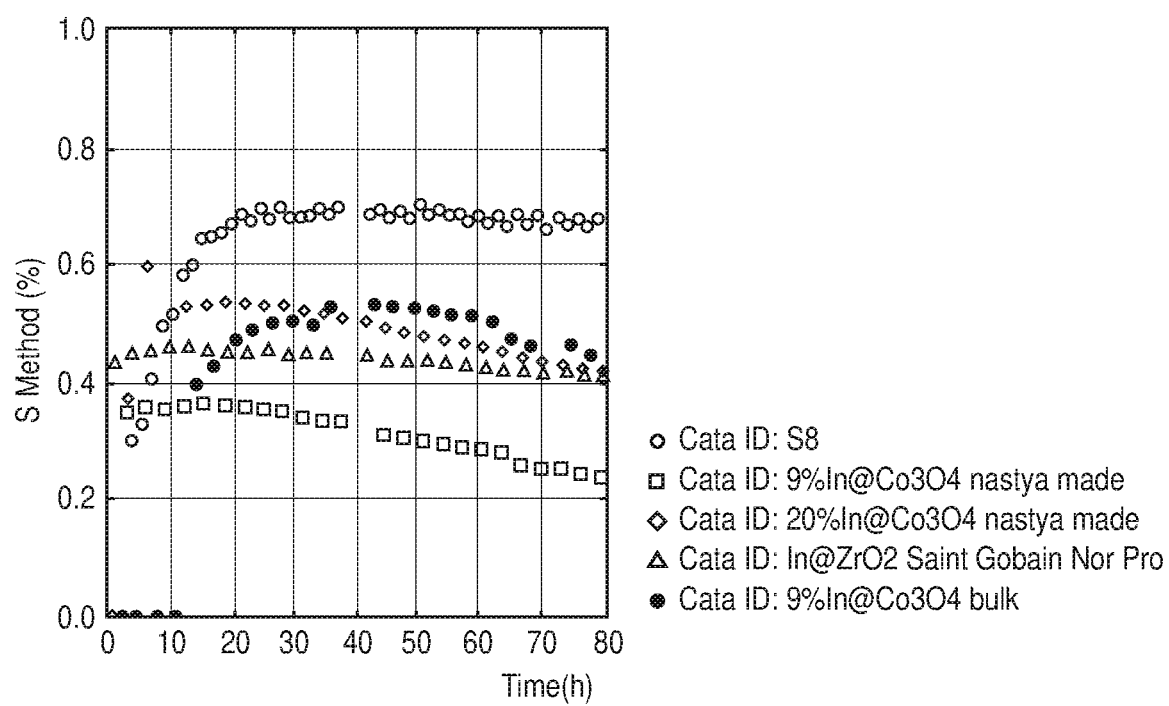
FIG. 10 is a graphical view showing a selectivity of the catalysts for methanol, according to one or more embodiments of the present disclosure.

FIG. 10 is a graphical view showing a selectivity of the catalysts for methanol, according to one or more embodiments of the present disclosure.

Example 7

In—Co Catalyst for Selective Carbon Dioxide Hydrogenation to Methanol

The direct hydrogenation of $CO_2$ to methanol using green hydrogen is regarded as a potential technology to reduce greenhouse gas emissions and reduce dependence on fossil fuels. For this technology to become feasible, highly selective and productive catalysts able to operate under a wide range of reaction conditions near thermodynamic conversion are required. The following Example demonstrates that indium in intimate contact with cobalt catalyzes the formation of methanol from $CO_2$ with high selectivity (>80%) and productivity (0.76 $g_{CH3OH} \cdot g_{catalyst}^{-1} \cdot h^{-1}$), at conversion levels close to thermodynamic equilibrium, even at temperatures as high as 300° C. and at moderate pressures (50 bar). The studied In@Co system, obtained via co-precipitation, underwent in-situ transformation under reaction conditions to form the active phase. Extensive characterization demonstrated that the active catalyst was comprised of a mixed metal carbide $Co_3InC_{0.75}$, indium oxide $In_2O_3$ and metallic Co.

Capture and utilization of carbon dioxide, the primary greenhouse gas, is of primary importance. Hydrogenating $CO_2$ into a valuable feedstocks using green hydrogen offers the possibility to directly sequester this greenhouse gas into a highly demanded utility chemicals. Among the potential products, methanol is a very interesting chemical platform and, also, a clean fuel. Sustainable methanol production requires sources of renewable hydrogen, inexpensively captured carbon dioxide and an efficient and highly selective catalyst. Clean routes to produce renewable $H_2$ by means of solar energy, hydro-, wind power or biomass are reported to be feasible to the day of today, while efficient carbon capture technologies require more advances.

A handful of catalysts for the transformation of carbon dioxide to methanol has been documented. Photo- and electrocatalytic systems advanced significantly over the last decades, but their performance is still rather low. The field recently achieved photothermal $CO_2$ hydrogenation using $In_2O_{3-x}(OH)_y$ with 50% selectivity to methanol and 0.06 mmol $g_{cat}^{-1} h^{-1}$ productivity. The vast majority of studies on homogeneous systems are focused on indirect transformations, such as hydrogenation of formates, carbonates or urea, disproportionation of formic acid or cascade multi-step catalysis. Direct homogeneous $CO_2$ hydrogenation is more difficult to achieve, but several catalysts were reported in recent years. Most of the reported systems operate at relatively mild conditions (125-165° C.) but, except from some notorious cases, most catalysts are based on noble metals and/or expensive phosphine ligands.

Since Imperial Chemical Industries developed the first heterogeneous catalyst for methanol synthesis from a mixture of synthesis gas and $CO_2$ (Cu—ZnO—$Al_2O_3$), research focus stirred into investigation of this material. It is now believed that it is copper that provides the active sites for carbon dioxide hydrogenation, resulting in 79% of reports published on this topic being about Cu based catalysts. The ternary Cu—ZnO—$Al_2O_3$ system, however, is not perfect—its selectivity to methanol is limited, due to the competing reverse water gas shift reaction (RWGS), moreover, stability issues arise when pure $CO_2$ is hydrogenated. Therefore, this reference catalyst needs to be operated at lower temperatures (<250° C.) and higher pressures (70 bar). Still under these conditions, a large part of the product stream needs to be recycled to convert the produced CO into MeOH. This results in high compressor and cooling costs and low per-pass productivity. Catalysts that can maintain good methanol selectivity at higher temperatures and lower pressures will help economics and also facilitate potential coupling to processes as MTO, typically operated at higher temperatures. Palladium was employed by several research group in order to find a replacement for copper. There, Ga promoted systems had the most of success. Other metal supported catalysts and bimetallic systems were also found to be active, such as Au/ZnO (0.42 $g_{MeOH}$ $g_{Au}$ $h^{-1}$, ca. 40% selectivity to MeOH under 5 bar, 240° C., conversion 15%), Ni—Ga (ca. 0.1 $g_{MeOH}$ $g_{catalyst}$ $h^{-1}$ under 1 bar and 200° C., selectivity ca. 100%, could not find conversion level), $In_2O_3/ZrO_2$ (ca. 0.3 $g_{MeOH}$ $g_{catalyst}$ $h^{-1}$ at 50 bar and 300° C., selectivity ca. 100%, conversion 5%), and ZnO—$ZrO_2$ (0.73 $g_{MeOH}$ $g_{catalyst}$ $h^{-1}$, methanol selectivity of up to 86 to 91% with $CO_2$ single-pass conversion of more than 10% under 50 bar, and 320°-315° C.).

This Example relates to and describes the preparation, characterization and performance of a novel highly selective catalyst based on In and Co. The initial solid was comprised of $In(OH)_3$ supported on $Co_3O_4$ and was prepared via co-precipitation. This solid, however, was better described as a precatalyst, since it undergoes severe transformation during the first reaction hours. After this induction period, the catalyst was formed and found to be mainly comprised of metallic Co (fcc), mixed metal carbide $Co_3InC_{0.75}$ and $In_2O_3$.

Methods

Catalyst preparation. The starting materials were cobalt acetate ($Co(CH_3COO)_2 \cdot 6H_2O$) and indium acetate ($In(CH_3COO)_3$), water, hydrogen peroxide and ammonia hydroxide solution. Both salts were dissolved in water and added dropwise to the stirred aqueous solution of $H_2O_2$ and $NH_4OH$. The mixture further underwent a hydrothermal treatment at about 180° C. for about 8 hours. The obtained powder, denoted as In@Co, was recovered, washed and subsequently dried at about 60° C. The compositional, textural, and structural properties of the In@Co catalyst were investigated by powder X-ray diffraction, high-resolution transmission electron microscopy, electron energy-loss spectroscopy, temperature-programmed reduction with $H_2$, X-ray photoelectron spectroscopy. $CO_2$ hydrogenation was performed over undiluted catalysts using a 16 parallel reactor system Flowrence®. Prior to the reaction, the In@Co catalyst was preheated in $N_2$ at about 300° C. and about 1 bar for about 1 h. Further details on catalyst preparation, characterization, and testing are given in the Supporting Information section below.

Results

Multiple preparation methods were investigated for the synthesis of In@Co solids, namely: precipitation, incipient wet impregnation, and ball milling (Tables S1-S2) (cf. supplementary information below). All prepared solids showed similar trends in terms of methanol selectivity during carbon dioxide hydrogenation. However, among all synthesized catalysts, those prepared by reverse co-precipitation provided the highest methanol productivity and the lowest $CH_4$ selectivity (cf. Table S3). For that particular reason, the study described herein focused on the latter preparation method. A series of catalyst was prepared with the different indium content. The precatalyst containing 20 wt % of indium was found to display the best performance and is denoted in the further text as In@Co-1.

Figure 11:
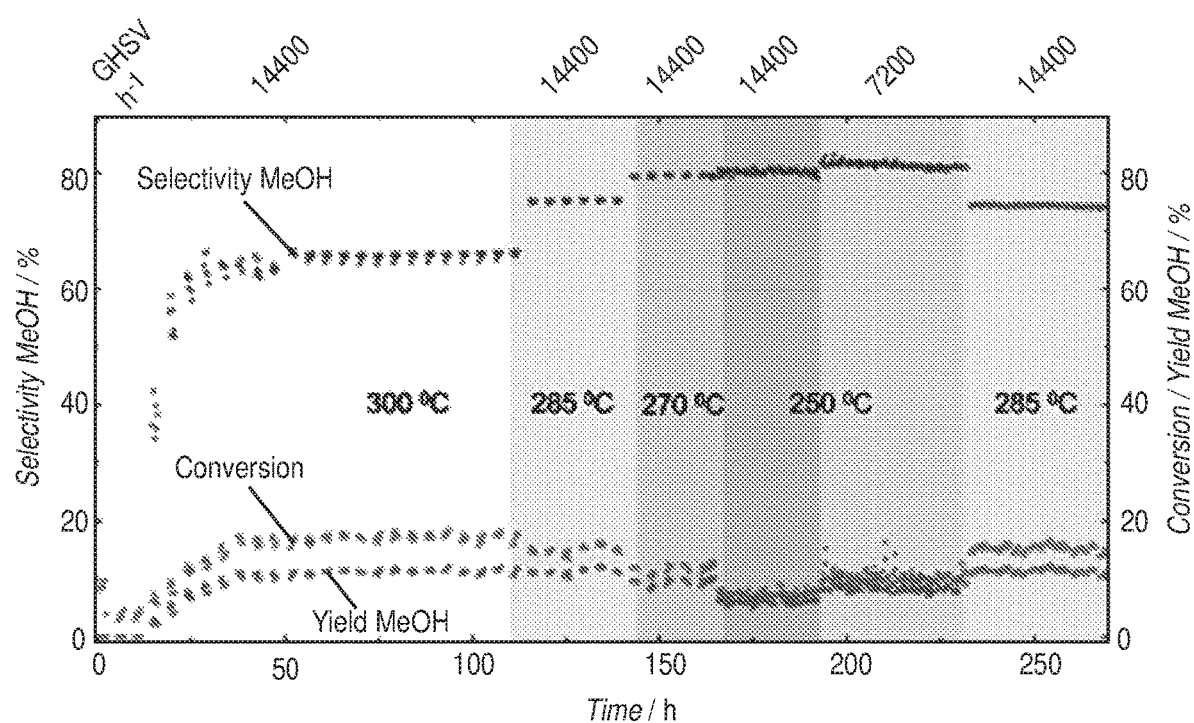
FIG. 11 is a graphical view showing methanol selectivity, yield and $CO_2$ conversion over In@Co catalyst at different temperatures and feed flows (Reaction conditions (unless otherwise is stated in the Figure itself) are 300° C., 50 bar, 20% $H_2$ 80% $CO_2$ feed, 50 mg of catalyst, 34.9 wt % In (in the spent catalyst)), according to one or more embodiments of the present disclosure.
Figure 12B:
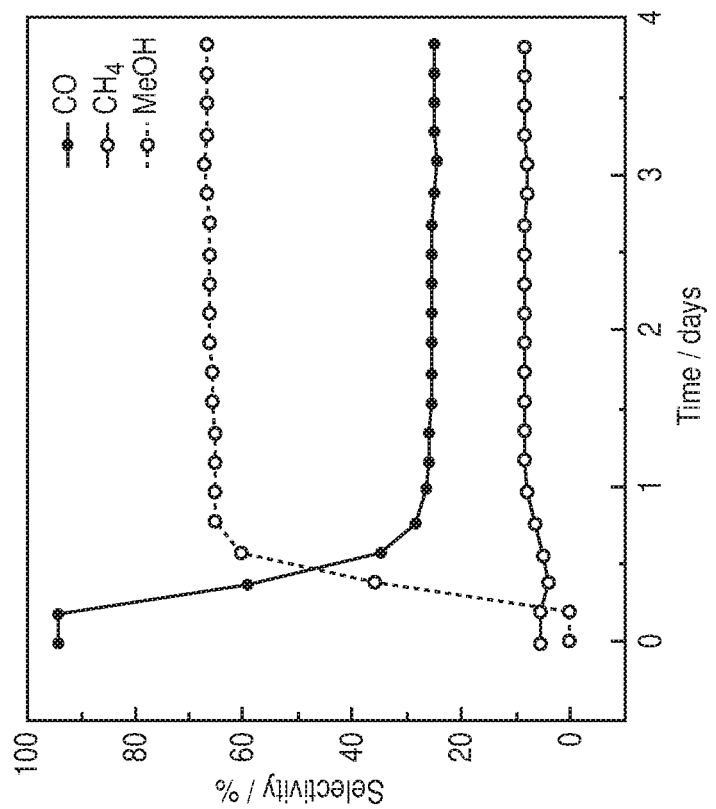
FIGS. 12A-12B is a graphical view showing a) Methanol productivity and selectivity over In@Co catalyst (orange) and Cu—ZnO—$Al_2O_3$ commercial catalyst from Alfa Aesar (green) and b) selectivities to different products (Reaction conditions are 300° C., 50 bar, 20% $H_2$ 80% $CO_2$ feed, 50 mg of catalyst, 34.9 wt % In, WHSV 2), according to one or more embodiments of the present disclosure.
Figure 12A:
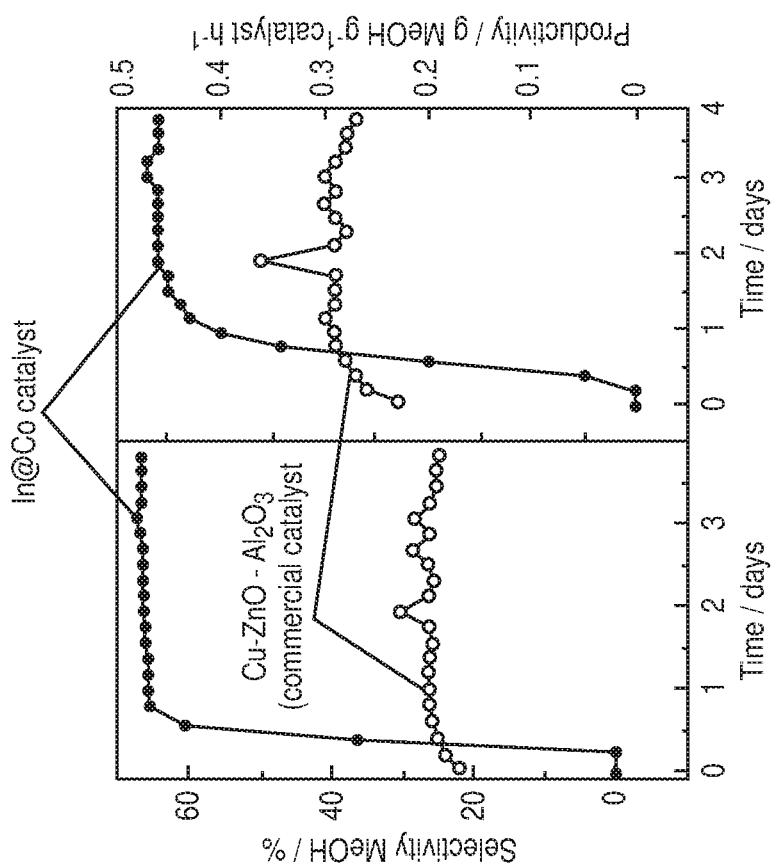

Catalytic performance. The In@Co-1 solid was tested for $CO_2$ hydrogenation from about 270 h at about 300° C. and about 50 bar (FIG. 11). The results showed an initial induction period of about 30 h followed by stable performance reaching a $CO_2$ conversion of about 19%. The prevalent product was methanol ($S_{MeOH}$=69%), with a limited formation of carbon monoxide ($S_{CO}$=23%) and methane ($S_{CH4}$=8%) as byproducts (FIGS. 12A-12B). Under the same experimental conditions, the commercial Cu—ZnO—$Al_2O_3$ catalyst had no induction period but displayed a much lower selectivity to methanol ($S_{MeOH}$=25%). Comparison of methanol productivity at the steady state—0.45 vs. 0.27 $g_{MeOH}$ $g_{catalyst}^{-1}$ $h^{-1}$ for In@Co-1 and Cu—ZnO—$Al_2O_3$, respectively—highlighted a vast improvement of the catalytic performance From these results, it was clear that activity of the Cu system in the undesired RWGS reaction was much higher than for the Co—In system.

Structural rearrangement during the catalytic test. The observation of a long induction period is usually a clear indication that the active catalytic phase forms under reaction conditions. Furthermore, a strong pyrophoric behavior of the final In@Co-1 catalyst was observed. Hence, the structural characterization of the spent catalyst was conducted with appropriate precautions to avoid any air exposure (details in supplementary information below). In the following part, the structural rearrangements subsequent to $CO_2$ hydrogenation are presented in detail.

Figure 13:
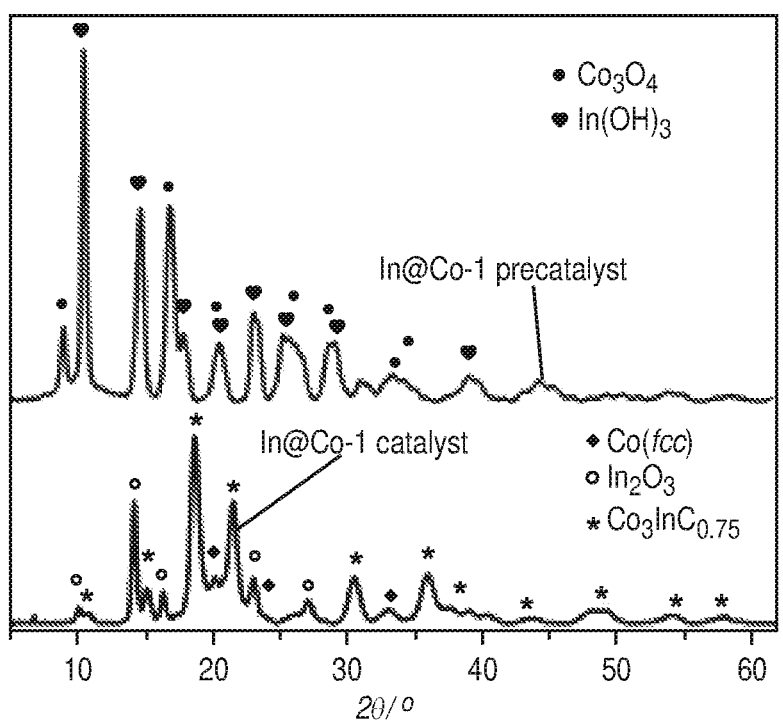
FIG. 13 is a graphical view of powder XRD patterns of the In@Co-1 solid before and after reaction acquired in transmission with flamed sealed capillaries and using an Mo Kα radiation as X-ray source, where the assignment of the main reflections is labeled as follow: * $Co_3O_4$, ♥ $In(OH)_3$, ♣ $Co_3InC_{0.75}$, ♦ Co(fcc), ● $In_2O_3$, according to one or more embodiments of the present disclosure.

The reverse coprecipitation with a metal solution including both $In(CH_3CO_2)_3$ and $Co(CH_3CO_2)_2$ salts and an ammonia solution as precipitation agent, followed by hydrothermal treatment, produced initially a mixture of dzhalindite ($In(OH)_3$) and cobalt (II, III) oxide ($Co_3O_4$) as nanoparticles. This was easily identified on FIG. 13 by considering the ensemble of d-spacings observed by powder X-ray diffraction (PXRD). The precipitation was nearly quantitative with a synthesis yield of 61% based on indium and 59% based on cobalt.

The nitrogen adsorption-desorption isotherm of the In@Co-1 precatalyst (FIGS. 14A-14C) was in-between a type II and IV isotherm according to the IUPAC classification. This type of isotherm was characteristic of mesoporous/macroporous solids. In@Co-1 precatalyst had a low specific surface area of 30 $m^2$ $g^{-1}$.

Figure 15A:
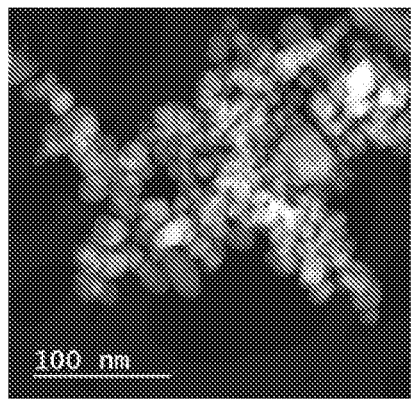
FIGS. 15A-15D shows ADF-STEM imaging and elemental mapping of the In@Co-1 catalyst before reaction: a) nanoparticles of $Co_3O_4$, b) nanoparticles of $In(OH)_3$, and c) $Co_3O_4$ nanoparticles trapped in amorphous indium hydroxide phase and d) superposition of Co (green), In (blue) and O (red) elemental maps of the same area, according to one or more embodiments of the present disclosure.
Figure 15B:
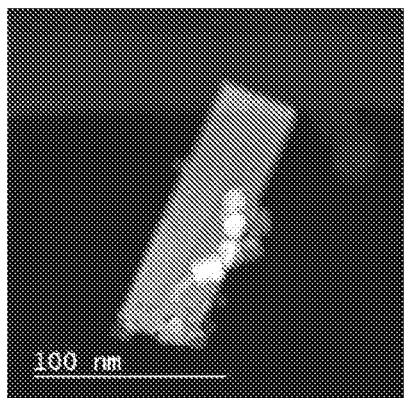
Figure 15C:
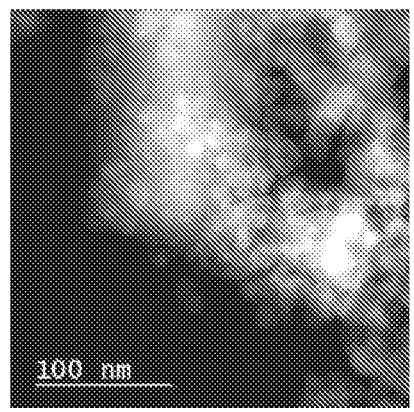
Figure 15D:
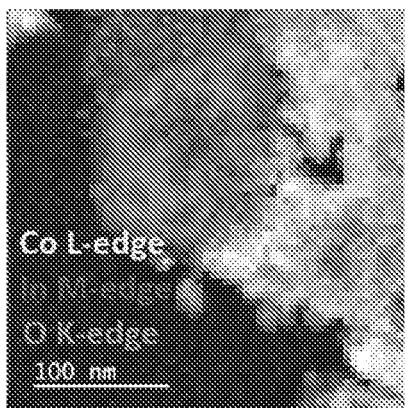

Imaging by ADF-STEM was used to investigate the morphological properties of the In@Co-1 catalyst before reaction. The micrograph presented in FIGS. 15A-15D shows a typical example of agglomerates containing $Co_3O_4$ roundish nanoparticles in the 10-40 nm range, and larger $In(OH)_3$ nanoparticles shaped as rectangular parallelepiped (>100×50 nm). Furthermore, Co and In elemental maps computed from EELS spectroscopy revealed that some of the $Co_3O_4$ aggregates were sometimes filled or trapped within an amorphous indium hydroxide phase (FIGS. 15C-15D).

Figures 16A, 16B, 16C:
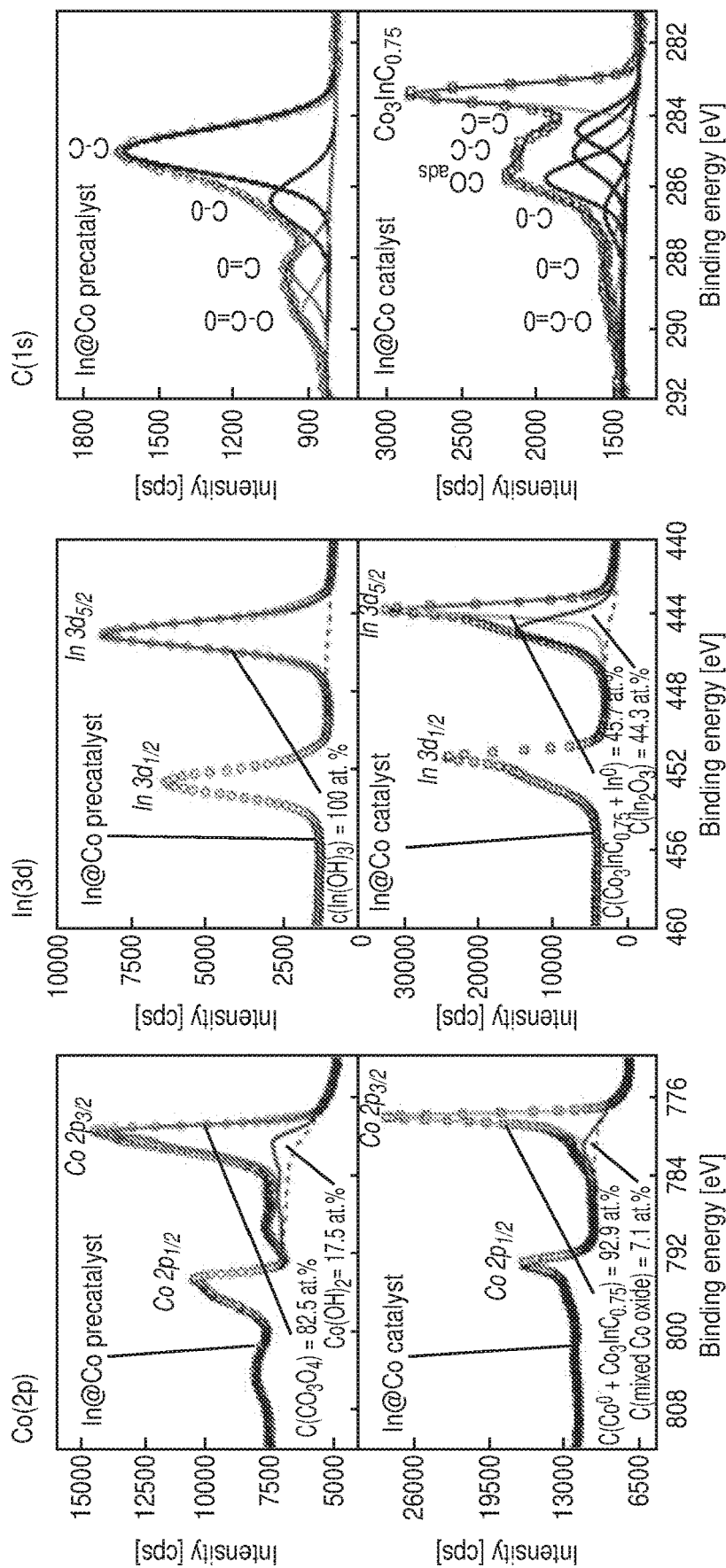
FIGS. 16A-16C shows high resolution X-ray photoelectron spectroscopy study of the In@Co-1 solid before and after reaction with core-levels: a) Co(2p), b) In(3d), and c) C(1s), where the open symbols are the experimental data while the full lines are the components used for the decomposition of the spectra, according to one or more embodiments of the present disclosure.
Figure 17A:
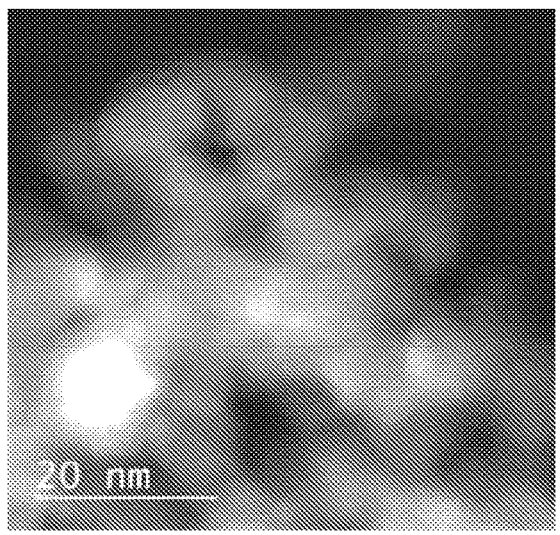
FIGS. 17A-17B shows ADF-STEM imaging and elemental mapping of metallic Co nanoparticles covered by an indium layer after reaction: (a) dark field imaging, b) colormix built with quantitative elemental maps computed from EELS spectroscopy data: Co (green), In (blue) and O (red), where the inset shows a line profile of the Co, O, and In atomic composition from the surface to the bulk (carbon edge taken into account during quantitative analysis), according to one or more embodiments of the present disclosure.
Figure 17B:
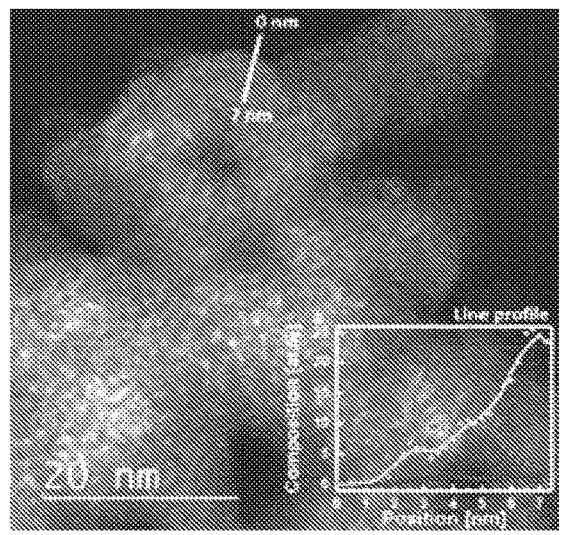

High resolution XPS spectrum of the Co 2p core level of the sample before reaction is shown in FIG. 16A (top). The spectrum had two main broad peaks at about 779.8 eV and about 794.9 eV corresponding to $2p_{3/2}$, $2p_{1/2}$ spin orbit lines, respectively. The spectrum also contained satellite structures at the high binding energy side of $2p_{3/2}$ and $2p_{1/2}$ main peaks, which indicated the existence of cobalt in oxide form. In order to identify the oxidation state of cobalt, peak fitting of Co $2p_{3/2}$ was conducted. The approach used for the peak fitting was similar to the one used by others, i.e., fitting of a broad main peak combined with the satellite structure. A Shirley background was applied across the Co $2p_{3/2}$ peak of the spectrum. The Co $2p_{3/2}$ from the sample before reaction in FIGS. 16A-16C was well fitted using a combination of the parameters derived from both $Co_3O_4$ and $Co(OH)_2$ standard samples. The results indicated that the sample contained 82.5% of $Co_3O_4$ and remaining 17.5% of the extra $Co^{2+}$ contribution. Since $Co(OH)_2$ was not detected by XRD, it was proposed that that this could be related to the presence of an amorphous Co hydroxide. The high resolution XPS spectrum of the In 3d core level (FIG. 16B, top) consisted of two main broad peaks at about 445.0 eV and about 452.6 eV corresponding to $3d_{5/2}$, $3d_{3/2}$ spin orbit lines respectively. The In $3d_{5/2}$ peak was fitted using a single component located at 445.0 eV attributed to $In^{3+}$ in $In(OH)_3$. FIGS. 17A-17B (top) shows the high resolution XPS spectrum of the C 1s core level of the sample. The C 1s core level from the sample before reaction was fitted using four components located at 285.0 eV, 286.4 eV, 288.3 eV and 289.5 eV corresponding to C—C/C—H (sp3), C—O, C═O and O—C═O bonds, respectively. Those contributions indicated that acetate anions remain adsorbed on the surface of In@Co solid despite extensive washing.

Figure 18A:
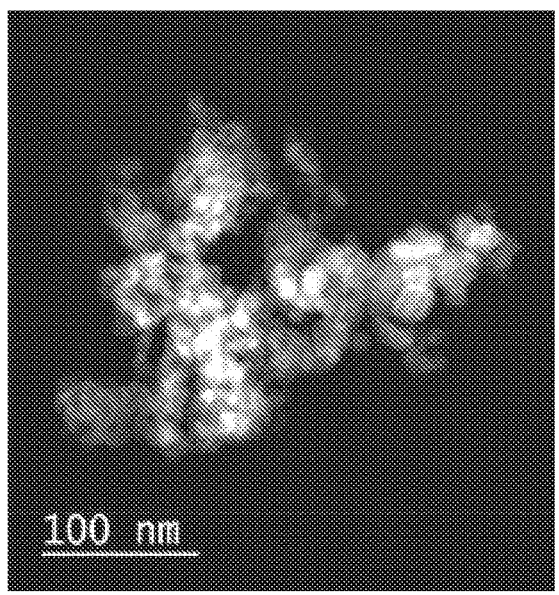
FIGS. 18A-18B shows ADF-STEM imaging and elemental mapping of the In@Co-1 catalyst after reaction operated a low magnification: a) dark field imaging, b) colormix built with elemental maps computed from EELS spectroscopy data: Co (green), In (blue) and O (red), according to one or more embodiments of the present disclosure.
Figure 18B:
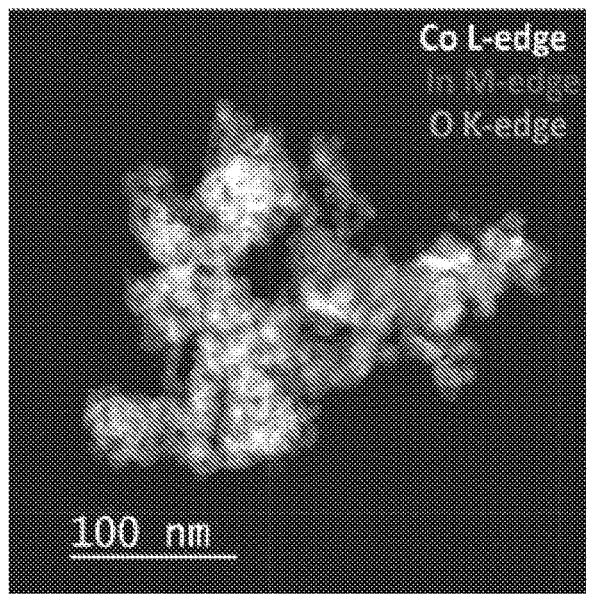

After $CO_2$ hydrogenation, large changes in phase composition, and morphological properties were observed although textural properties remain comparable ($S_{BET}$(pre-catalyst)=30 $m^2/g$ vs. $S_{BET}$ (catalyst)=17 $m^2/g$). Let's first consider the crystalline phases in the In@Co-1 catalyst (FIGS. 18A-18B). All of the indium hydroxide converted into indium oxide ($In_2O_3$) by dehydration. The thermal decomposition occurred likely during the pre-heating under $N_2$ at 300° C., because this transformation is known to take place around 220° C. Additionally, the cobaltosic oxide transformed into metallic Co that crystallized in a face-centered cubic crystal system. However, the most striking evolution was the appearance of a mixed metal carbide with the $Co_3InC_{0.75}$ stoichiometry as the major crystalline phase in the spent catalyst. Note also that none of the reported Co—In intermetallic compounds ($CoIn_2^{31}$, $CoIn_3^{32}$) or pure metallic indium was detected.

Figure 19A:
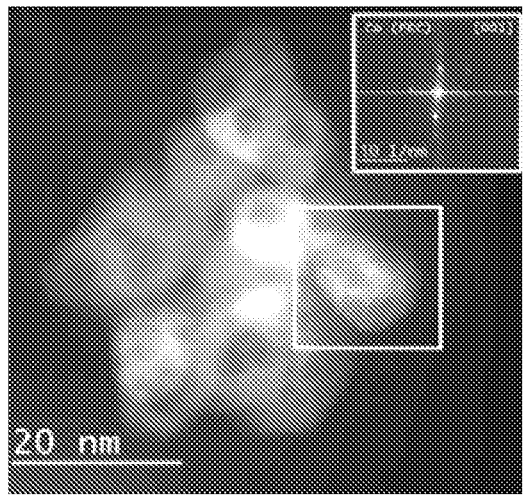
FIGS. 19A-19D shows ADF-STEM imaging and elemental mapping of the In@Co-1 catalyst after reaction: a) nanoparticles of metallic Co (fcc) with one crystallite observed along the [001] zone axis, with b) its respective elemental mapping which highlight that only Co is detected, where conversion of the former $In(OH)_3$ nanoparticles into $In_2O_3$: c) imaging and d) elemental mapping (superposition of Co (green), In (blue) and O (red) maps), according to one or more embodiments of the present disclosure.
Figure 19B:
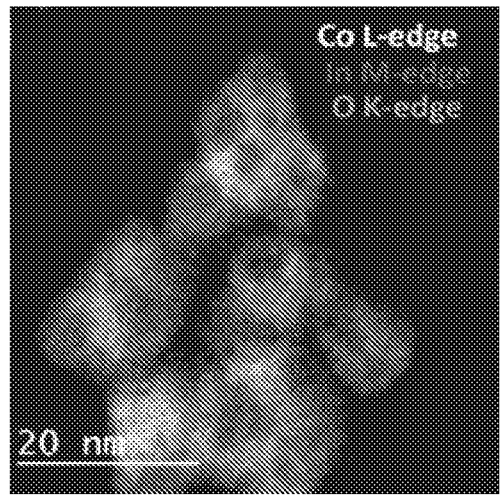
Figure 19C:
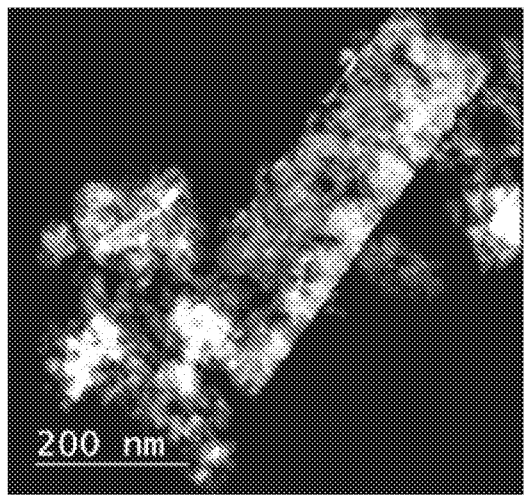
Figure 19D:
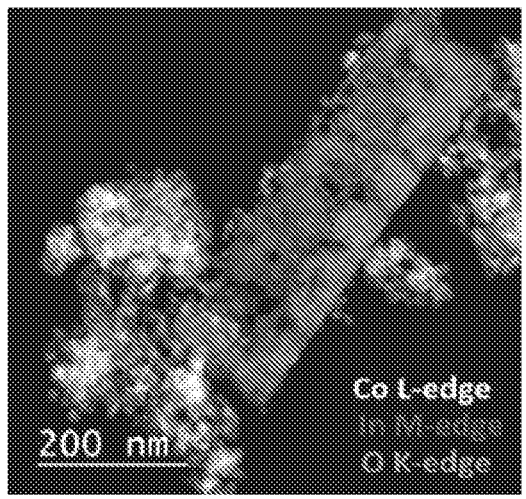

The fate of each phase in the pre-catalyst was also characterized after $CO_2$ hydrogenation using ADF-STEM imaging and EELS spectroscopy (FIGS. 18A-18B). The large and rectangular $In(OH)_3$ nanoparticles were converted into much smaller $In_2O_3$ crystallites (FIGS. 19A-19B and purple color in FIG. 18B). The $Co_3O_4$ nanoparticles were transformed into metallic Co nanoparticles (FIGS. 19C-19D and green color in FIG. 18B. The previous aggregates of $Co_3O_4$ nanoparticles, which were in contact with amorphous indium hydroxide, were likely the starting precursor for the formation of $Co_3InC_{0.75}$ carbide (cyan color in FIG. 18B). Interestingly, there was also a new component in the spent catalyst that was often observed but cannot be detected by X-ray diffraction. This is illustrated on FIGS. 18A-18B using ADF-imaging at high magnification (FIG. 18A), where some metallic Co nanoparticles are decorated with a lighter material. Quantitative analysis of the EELS spectroscopy data (details in supplementary information) indicated this was due to the formation of an oxidized indium-cobalt layer with a range of thickness between 1 and 4 nm (FIG. 18B). This surface layer included irregular amount of oxygen through the sample and still contained much more cobalt than indium atoms (minimum Co/In ratio measured≈2.5).

Surface characterization by XPS suggested that the surface state was also heavily modified after reaction. The elemental composition (FIGS. 20A-20B) evolved with a decrease of the oxygen content from 49.9 at. % down to 20.5 at. % and a simultaneous increase of the carbon content from 13.2 at. % up to 24.6 at. %. This result was consistent with the formation of the mixed $CoInC_{0.75}$ carbide and the remaining presence of $In_2O_3$. On the other hand, the Co/In ratio decreased spectacularly from 6.5 down to 2. On overall, it meant that the In@Co solids rearranged during $CO_2$ hydrogenation to present more indium on its surface, also in accordance with the former TEM observations. FIG. 17A shows the high resolution XPS spectrum of the Co 2p core level of the sample after reaction. The Co $2p_{3/2}$ was well fitted using a combination of the parameters derived from cobalt metallic and mixed cobalt oxides from standard samples. The dominant Co $2p_{3\;1\;2}$ was located at 778.2 eV corresponds to metallic cobalt or/and cobalt carbides, whereas the broad peak centered around ~781.1 eV corresponds to cobalt mixed oxides. The In@Co catalyst still contained about 7.1% of oxidized cobalt atoms after the reaction. The In $3d_{5/2}$ peak was fitted using two components located at 443.7 eV and 444.7 eV attributed to indium in a metallic state or within the $CoInC_{0.75}$ carbide (55.7 at. %) and to indium in $In_2O_3$ (44.3 at. %).

It was very difficult to distinguish between metallic and carbide state considering only Co 2p and In 3d core levels since they had similar binding energy. In order to substantiate the presence of the metallic carbide using XPS spectroscopy, a high resolution spectrum at the $C_{1s}$ core level of the sample after reaction was recorded (FIG. 17C). The $C_{1s}$ core level from the sample after reaction was fitted using seven components located at 283.4 eV, 284.4 eV, 285.0 eV, 285.7 eV 286.7 eV, 288.2 eV and 289.6 eV corresponding to C—Co, C═C (sp2), C—C/C—H (sp3), CO—Co, C—O, C═O and O—C═O bonds. In comparison to In@Co pre-catalyst, the appearance of $CoInC_{0.75}$ carbide and the presence of both graphitic carbon and CO adsorbed on metallic cobalt was observed for the In@Co catalyst after the reaction.

Figure 21A:
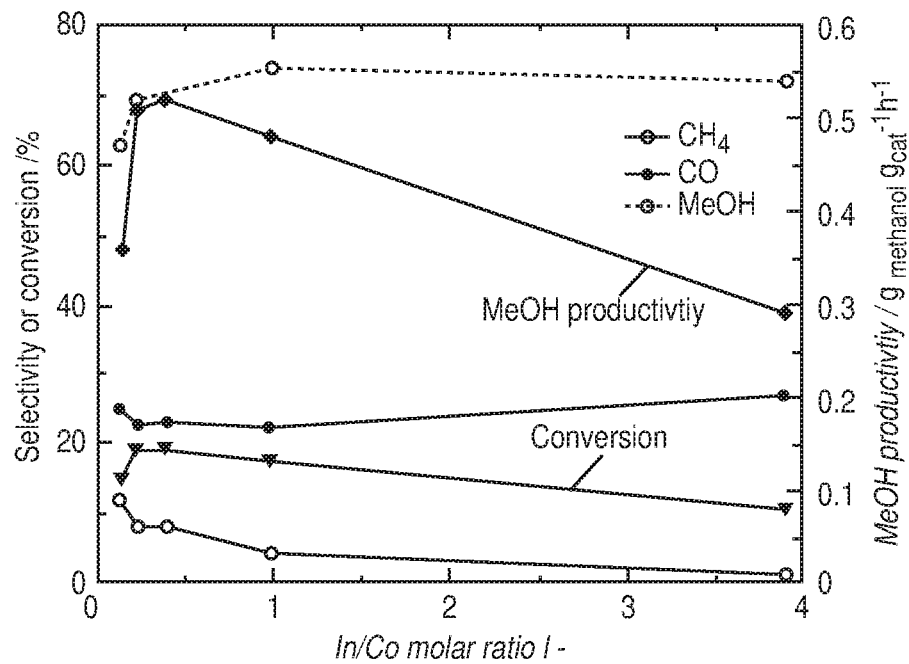
FIGS. 21A-21B is a graphical view of catalytic activity of a) In@Co-1 and b) In@Co-2 catalysts with a different indium to cobalt ratios, according to one or more embodiments of the present disclosure.
Figure 21B:
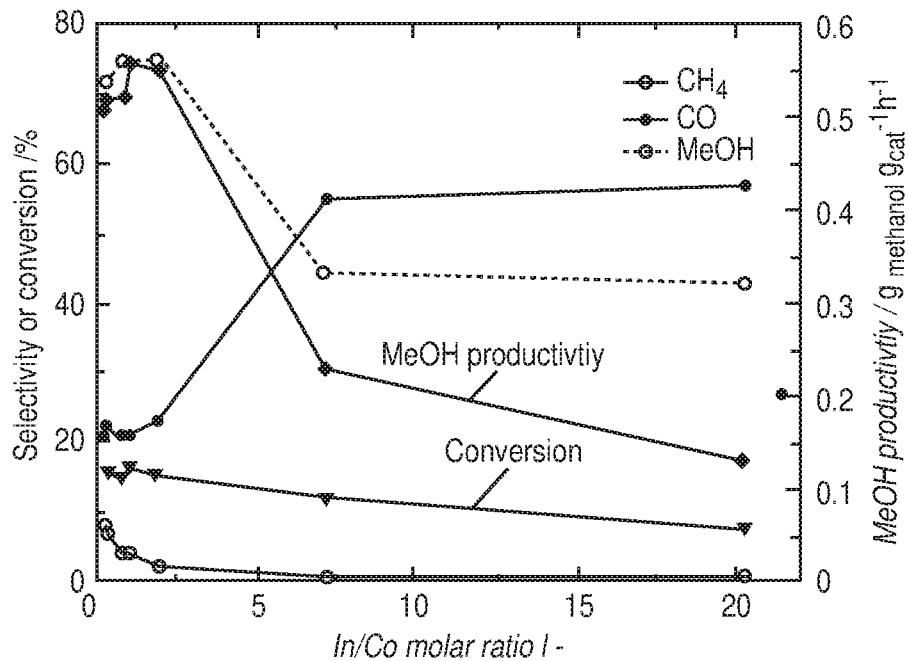
Figure 22A:
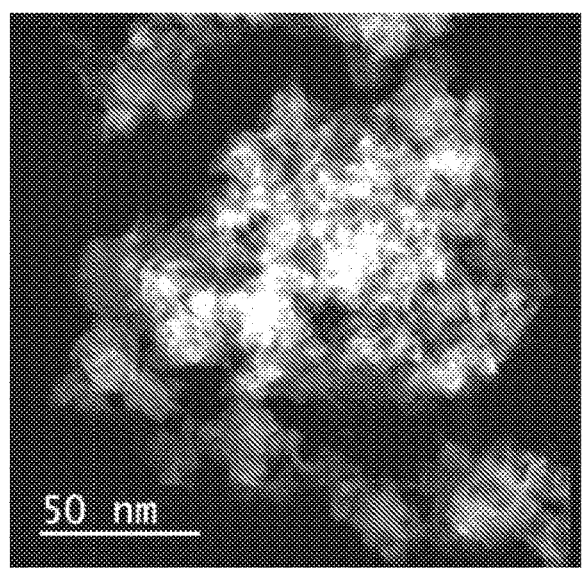
FIGS. 22A-22E shows ADF-STEM imaging and elemental mapping of the In@Co-2 catalyst before reaction: (a) dark field imaging, b) oxygen map, c) cobalt map, d) indium map, e) superposition of Co (green), In (blue) and O (red) elemental maps of the same area, according to one or more embodiments of the present disclosure.
Figure 22B:
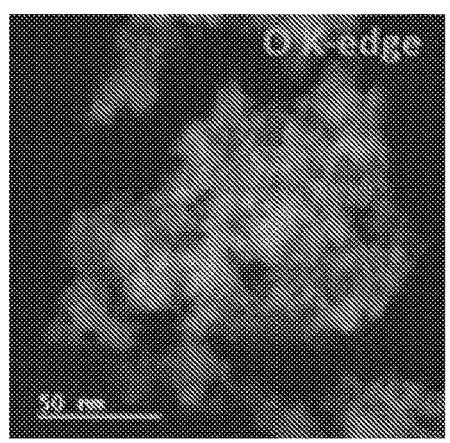
Figure 22C:
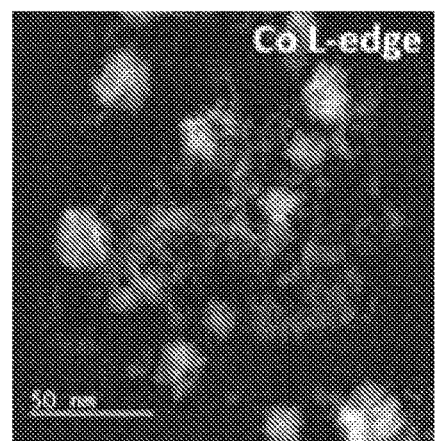
Figure 22D:
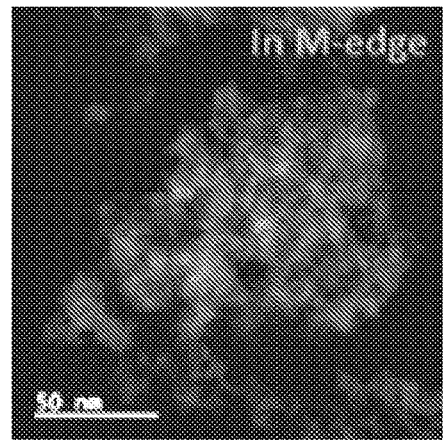
Figure 22E:
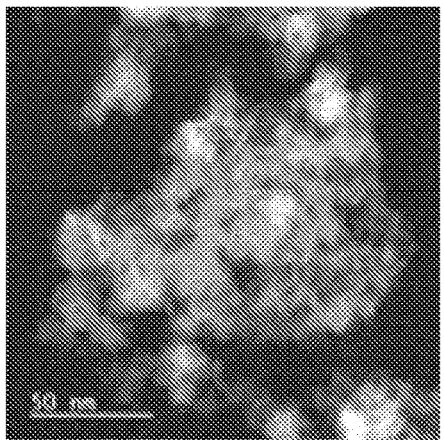

Unraveling the active catalytic phase. Knowing the composition of the In@Co-1 catalyst, catalytic tests with individual components and their physical mixtures were performed (Table S3). Cobalt oxide, once converted to metallic Co under reaction conditions, predictably converted carbon dioxide to methane with 100% selectivity. Pure $In_2O_3$ showed negligible conversion of ca. 1% with carbon monoxide as the only product. A pure $Co_3InCoC_{0.75}$ phase was obtained from Metal Organic Framework mediated synthesis via pyrolysis of a Co—In MOF (see SI). The resultant $Co_3InC_{0.75}$ carbide, alone or mixed with $In_2O_3$ in different proportions, did not produce any methanol as well, but CO. The systematic elimination of the former candidates suggested that the oxidized indium-cobalt layer around metallic cobalt was the active phase for the selective formation of methanol. Indeed, there are precedents in the literature where Ni, Co, Cu metal nanoparticles were alloyed with indium and tested for the selective hydrogenation of carboxylic acids to alcohols. When compared against the parent monometallic catalyst, a systematic suppression of the hydrodecarbonylation reaction was found. By analogy, it was proposed that indium poisoned the surface of metallic cobalt, hindering its total hydrogenation activity (cf. 80% $CO_2$ conversion on metallic Co vs. 19% on In@Co-1). However, this surface modification may have also prevented methane formation due to a slower hydrogenolysis rate of the C—O bond compared to the desorption rate of the CO and $CH_3OH$ intermediates. The influence of In content on the catalytic performance also supported this hypothesis. FIGS. 21A-21B show the catalytic behavior of catalysts that were prepared by the same method varying indium and cobalt content. The best performance was achieved on catalysts with a In/Co ratio of 0.38. Decreasing indium content in the solid leads to higher yield of the undesired methane—in this case the surface of metallic cobalt would be less perturbed by the presence of indium and thus could eventually achieve the complete hydrogenation of carbon dioxide. On the other hand, with high indium content, selectivity towards methane dropped to about 1%, together with a drastic decrease of conversion (19% vs. 11%).

Optimization of the catalyst formulation. Despite its promising performances, the first In@Co-1 catalyst had important heterogeneity, due to significant amounts of $In_2O_3$ and $Co_3O_4$ phases that did not contribute to the selective formation of methanol. It was hypothesized that the heterogeneity after the induction period arose mainly from the initial one in the pre-catalyst. Reaching a better mixing of indium and cobalt in the as-synthesized solid was expected to enhance the formation of the relevant active phase. To this end, the hydrothermal treatment used for the previous preparation of In@Co-1 samples was omitted to avoid segregation of the $In(OH)_3$ and $Co_3O_4$ phases. Hence, a second series of catalysts at varying In/Co ratios was prepared and denoted as In@Co-2.

Figure 23:
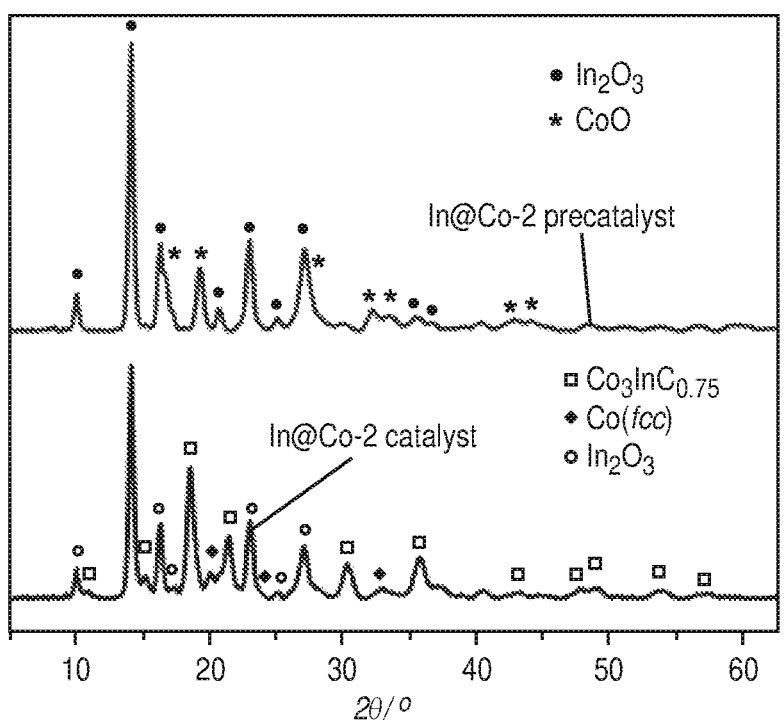
FIG. 23 shows powder XRD patterns of the In@Co-2 solid with a In/Co molar ratio equal to 1 before and after reaction acquired in transmission using an Mo Kα radiation as X-ray source, where the assignment of the main reflections is labeled as follow: * CoO, ♣ $Co_3InC_{0.75}$, ♦ Co(fcc), ● $In_2O_3$, according to one or more embodiments of the present disclosure.

The In@Co-2 pre-catalyst was composed of an intricate mixture of Co and In atoms with some crystalline and amorphous components as observed by ADF-STEM/EELS (FIGS. 22A-22E). The crystalline part was characterized by powder X-ray diffraction as a mixture of CoO and $In_2O_3$ nanoparticles (FIG. 23). Besides, the nitrogen adsorption-desorption isotherms of materials synthesized without hydrothermal treatment were type IV, typical of mesoporous solid (FIG. 12B). The specific surface area had markedly increased up to a range of 80-200 $m^2\ g^{-1}$ compared to the initial 30 $m^2\ g^{-1}$ of the In@Co-1 precatalyst. The crystalline phases after catalyst activation were also found to be a mixture of $Co_3InC_{0.75}$, $In_2O_3$ and Co(fcc) phases similarly to the In@Co-1 catalyst (FIGS. 22A-22E)

Figure 24:
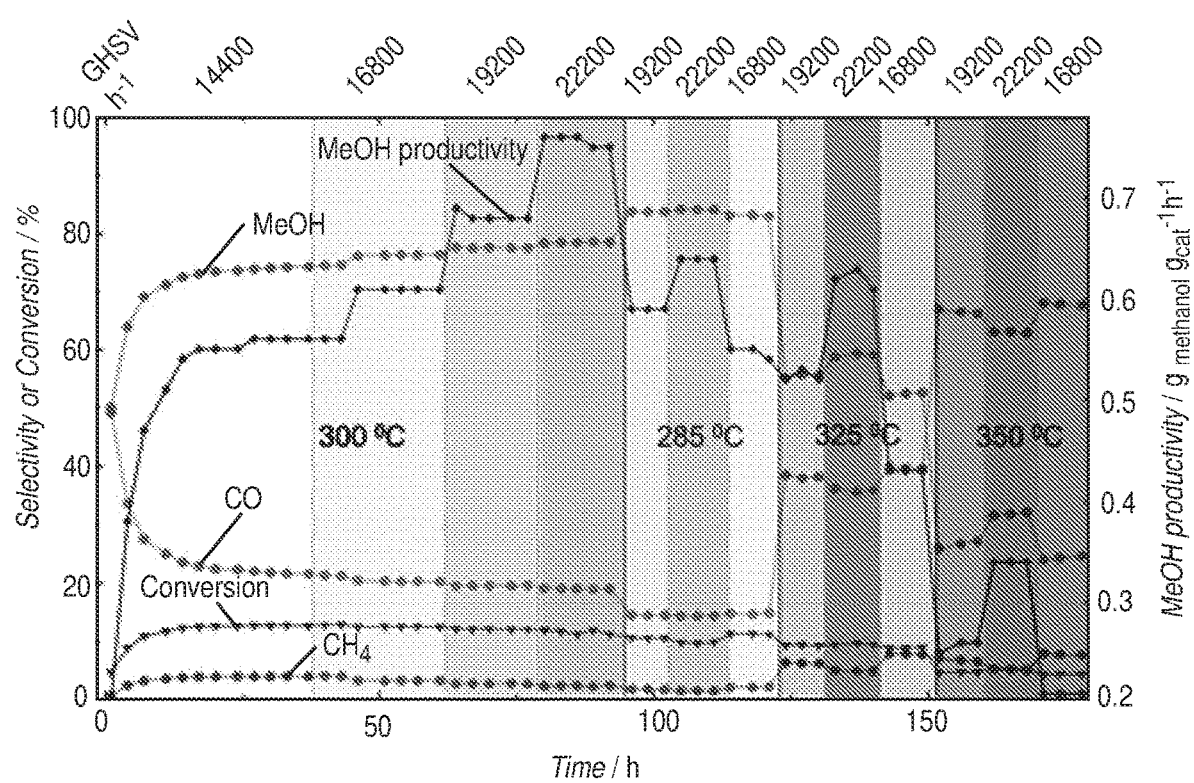
FIG. 24 is a graphical view of methanol selectivity, yield and $CO_2$ conversion over In@Co-2 catalyst at different temperatures and feed flows (Reaction conditions (unless otherwise is stated in the Figure itself) are 300° C., 50 bar, 80% $H_2$ 20% $CO_2$ feed, 50 mg of catalyst, 56.1 wt % In in the pre-catalyst), according to one or more embodiments of the present disclosure.

When applied in $CO_2$ hydrogenation, a similar effect of indium loading on the catalytic performance was observed (FIGS. 21A-21B). However, in this case, due to the better initial dispersion of In, a broader range for the optimum molar ratio In/Co was found. At the same time, both higher productivities and selectivities were observed. A catalytic run with the In@Co-2 catalyst (In/Co=1) was performed for 170 hours under the same chosen standard conditions of about 300° C. and about 50 bar (FIG. 24). The results showed the same period of about 30 h followed by stable performance reaching a $CO_2$ conversion of about 6%. The selectivity of methanol reached about 75%, with a limited formation of carbon monoxide ($S_{CO}$=21%) and methane ($S_{CH4}$=4%). Increasing the GHSV from 14400 $h^{-1}$ to 22200 $h^{-1}$ the selectivity towards methanol reached about 79% with drop of the selectivity towards methane from 4 to 2.3%. That equals to the methanol productivity of 0.76 $g_{MeOH}\ g_{cat}^{-1}\ h^{-1}$. Further decrease in temperature to 285° C. can deliver selectivities to methanol in the order of 85% with a negligible formation of the undesired methane. It had to be noted that increasing the feed flow even further, productivity of 0.86 $g_{MeOH}\ g_{cat}^{-1}\ h^{-1}$ can be achieved at GHSV 27500 $h^{-1}$ and standard conditions.

Figure 25:
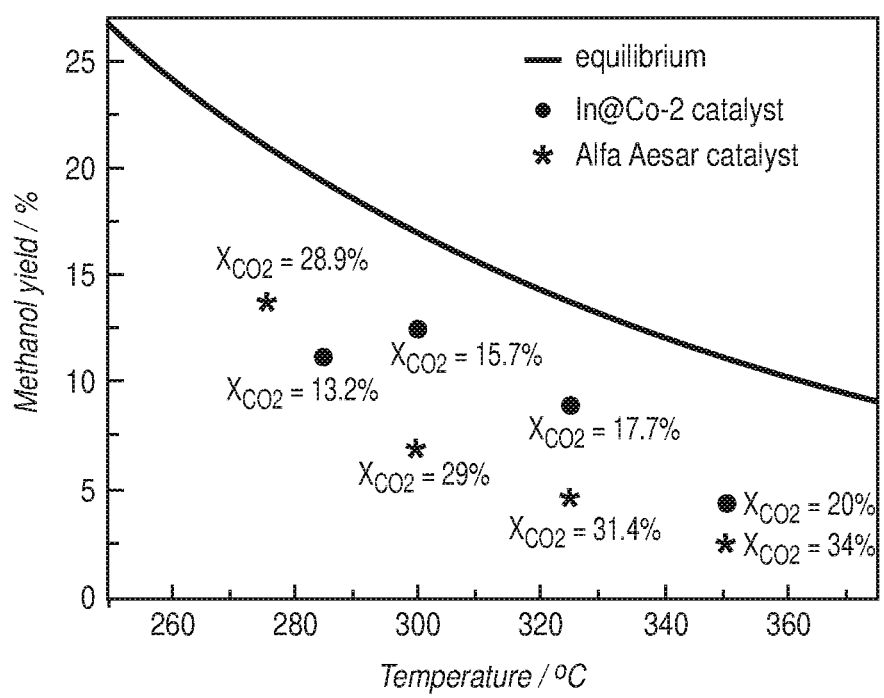
FIG. 25 is a graphical view showing comparison of the In@Co-2 system to the conventional Cu based catalyst from Alfa Aesar (Reaction conditions 50 bar, 80% $H_2$ 20% $CO_2$ feed, 50 mg of In@Co-2 catalyst, 56.1 wt % In in the pre-catalyst), according to one or more embodiments of the present disclosure.
Figure 26A:
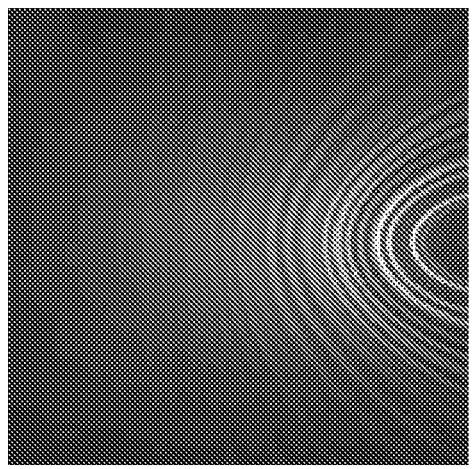
FIGS. 26A-26D shows 2D frames collected in transmission mode with flamed sealed capillaries and using an Mo Kα radiation as X-ray source for Co@In-1 solids a) before reaction and b) after reaction and for Co@ In-2 solids c) before reaction and d) after reaction, according to one or more embodiments of the present disclosure.
Figure 26B:
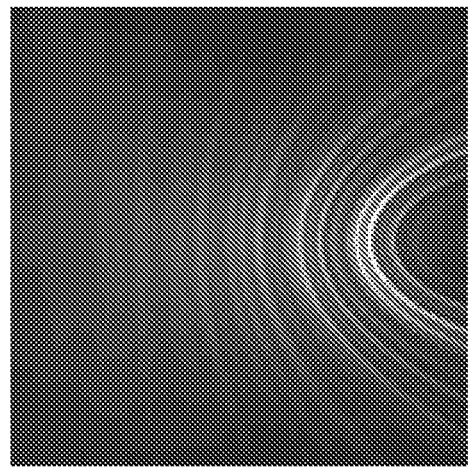
Figure 26C:
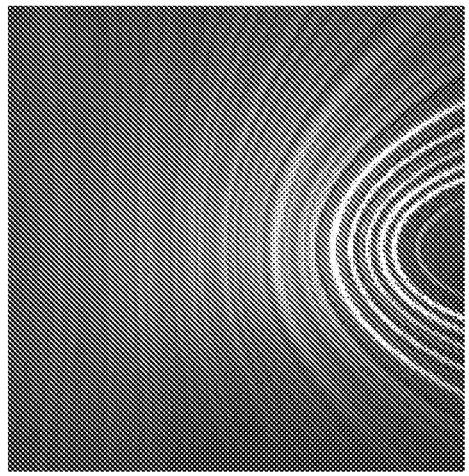
Figure 26D:
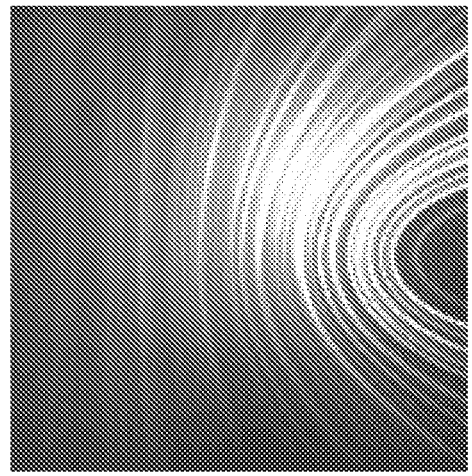
Figure 27A:
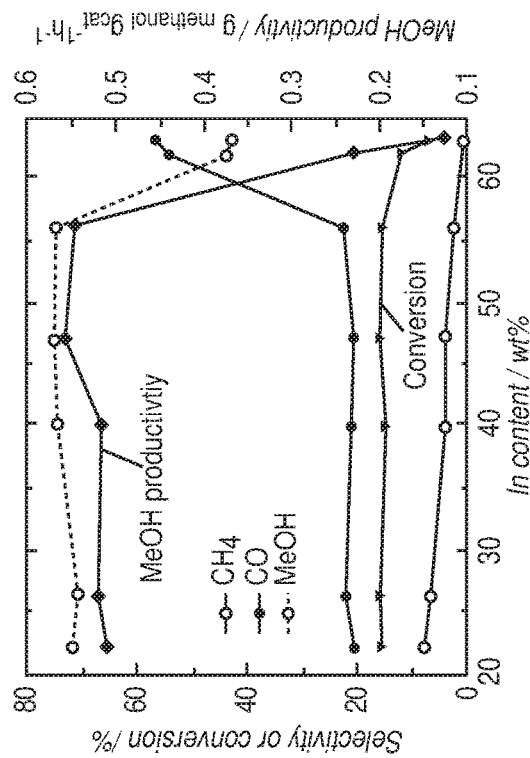
FIGS. 27A-27D is a graphical view of catalytic activity of a) In@Co-1 catalysts with a different indium content b) In@Co-2 catalysts with a different indium content c) In@Co-1 catalysts with a different cobalt content d) In@Co-2 catalysts with a different cobalt content, according to one or more embodiments of the present disclosure.
Figure 27B:
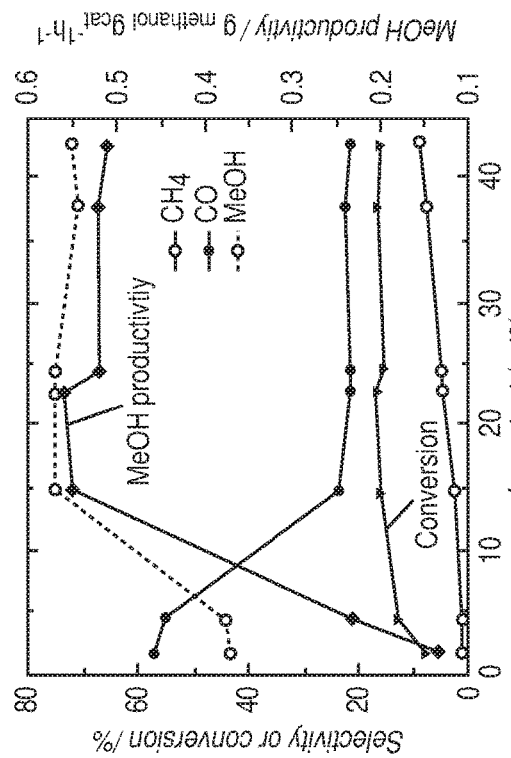
Figure 27C:
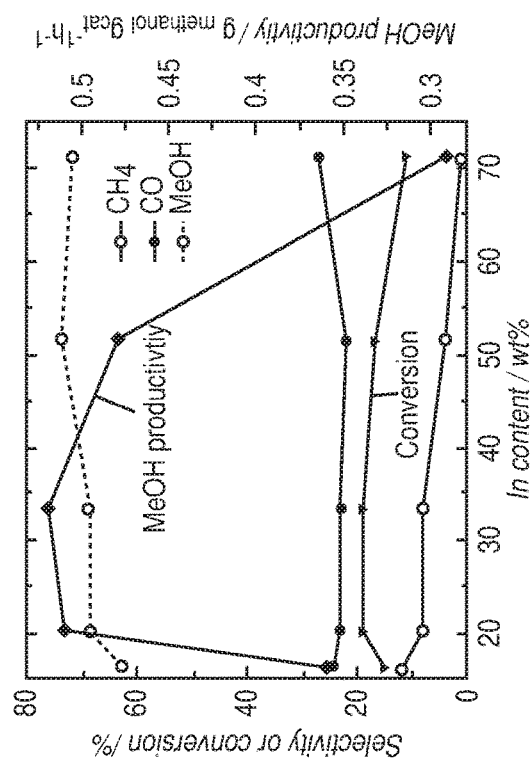
Figure 27D:
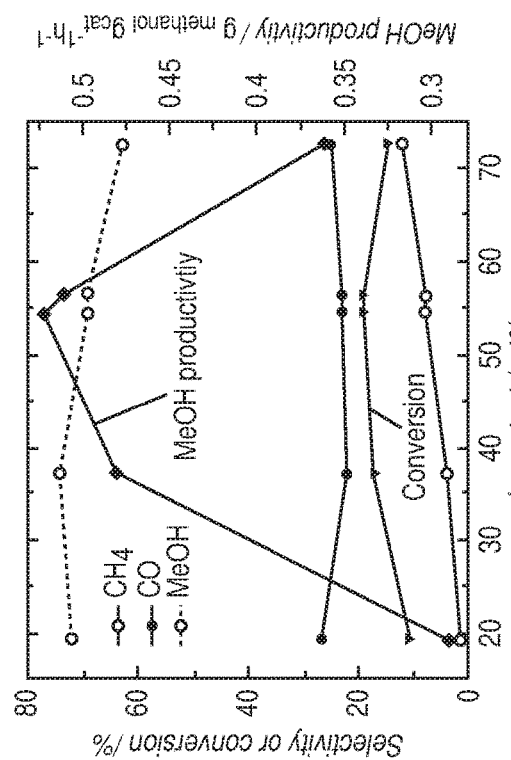

To extend the comparison between In@Co-2 and Cu—ZnO—$Al_2O_3$, the MeOH yield at 50 bar as plotted for temperatures ranging from about 250° C. to about 350° C. against thermodynamic equilibrium conversion (FIG. 25).

From this figure, it was easy to realize that the In@Co-2 system was able to maintain high methanol selectivities over a wider range of temperatures than the commercial Cu—ZnO—$Al_2O_3$, allowing in this way a much higher productivity per pass: up to 0.76 $g_{MeOH}/g_{cat}\ h^{-1}$ vs. 0.29 $g_{MeOH}/g_{cat}\ h^{-1}$ at GHSV 14400 $h^{-1}$. The value of 0.86 $g_{MeOH}/g_{cat}\ h^{-1}$ was obtained at higher feed flow. Even when compared with more recent developments (0.73 $g_{MeOH}/g_{cat}\ h^{-1}$ for ZnO—$ZrO_2$ catalyst at lower conversion level, the highest previously reported data), both in terms of yield per pass and productivity (vide supra), the reported In@Co catalyst sets a new state of the art.

In summary, a novel indium/cobalt based system was reported for methanol production from carbon dioxide. The catalyst showed high selectivity (up to 80%) to methanol at conversions close to thermodynamic equilibrium, outstanding stability and a record productivity. Different preparation methods lead to a similar catalyst composition which was formed in-situ under reaction conditions. The close vicinity of cobalt and indium was found to be key to catalytic performance Supporting Information Catalyst preparation. The catalyst denoted as In@Co-1 was obtained via co-precipitation method. The starting materials were cobalt acetate ($Co(CH_3COO)_2.6H_2O$) and indium acetate ($In(CH_3COO)_3.xH_2O$), water, hydrogen peroxide (23% solution in water) and 28% ammonia hydroxide solution as precipitation agent. A first about 3.49 g of $Co(CH_3COO)_2.6H_2O$ and about 1.02 g of $In(CH_3COO)_3$ were dissolved in about 35 ml of $H_2O$. Separately, about 1.39 mg of $H_2O_2$ and about 35 ml of ammonia hydroxide were diluted with $H_2O$ to about 315 ml of the total volume. In the next step, the salts containing solution was added to the stirred ammonia hydroxide solution drop by drop with the rate of 2 ml/min. The mixture further underwent a hydrothermal treatment at about 180° C. for about 8 hours within a 500 ml autoclave. The obtained powder, denoted as In@Co, was recovered and washed via centrifuging and subsequently dried at about 60° C. The catalyst denoted as In@Co-2 was obtained following the same procedure as for In@Co-2 but with the omitted hydrothermal treatment. The series of catalysts were prepared varying the cobalt acetate and indium acetate loadings (Table 1). In bold red there the catalyst with the best performance from each series are highlighted. The highlighted catalysts were chosen as model catalysts for further characterization.

As alternative catalyst preparation methods, wet impregnation and dry ball milling were performed. To obtain a catalyst by wet impregnation, about 50 ml of aqueous solution containing about 8.33 g of $In(NO_3)_3.xH_2O$ was prepared. The volume of about 0.36 ml of the solution was added to about 1 g of the carrier $Co_3O_4$, mixed and dried at about 60° C., repeated three times and subsequently calcined at about 450° C. To obtain a catalyst by ball milling, a ball bill vessel was charged with about 1 g of $Co_3O_4$, about 90 mg $In(NO_3)_3.xH_2O$ and about 20 g of zirconia beads; the mixture was ball milled with a planetary ball mill at 400 rpm for about 12 hours and subsequently calcined at about 450° C.

TABLE 1

| $Co(CH_3COO)_2\cdot 6H_2O$/ g | $In(CH_3COO)_3\cdot xH_2O$/ g | Molar In/Co ratio$_{In@Co-1\ series}$[a] | Molar In/Co ratio$_{In@Co-2\ series}$[a] |
|---|---|---|---|
| 4.18 | 0.255 | — | 0.26 |
| 3.95 | 0.51 | 0.13 | 0.57 |
| 3.49 | 1.02 | 0.22 | 0.84 |

TABLE 1-continued

| $Co(CH_3COO)_2 \cdot 6H_2O$/ g | $In(CH_3COO)_3 \cdot xH_2O$/ g | Molar In/Co ratio$_{In@Co\text{-}1\ series}$ [a] | Molar In/Co ratio$_{In@Co\text{-}2\ series}$ [a] |
|---|---|---|---|
| 3.3 | 1.275 | — | 1.05 |
| 3.08 | 1.32 | 0.38 | 1.94 |
| 2.2 | 2.55 | 0.98 | 7.2 |
| 0.87 | 4.09 | 3.9 | 20.2 |

[a] Obtained from ICP-OES results

Mixed indium cobalt carbide synthesis. The carbide $Co_3InC_{0.75}$ was obtained after pyrolysis of the modified CPM-470 Co—In MOF. In a 150 mL Durex bottle, a mixture of about 1.052 g of $In(NO_3)_3$, about 1.619 g of $Co(CH_3COO)_2.6H_2O$, about 1 g of terephthalic acid and about 0.946 g of 3,5-diamino-1,2,4-triazole was dissolved in about 80 mL of DMF, about 16 mL of water and about 0.6 mL of concentrated HCl. After sonication, the bottle was heated in a preheated oven at about 100° C. for about 3 days. After cooling down, solvent exchange was performed with ethanol for about 3 days and the purple crystals were recovered by filtration. Then, about 1 g of MOF was placed in a horizontal oven and heated at about 700° C. for about 8 h, after a heating rate of 1° C./min, under air flow of about 50 mL/min. It was cooled down to room temperature at a rate of 1° C./min. The resulting black powder was analyzed by PXRD where only the crystallized carbide $Co_3InC_{0.75}$ can be indexed.

Carbon dioxide hydrogenation to methanol. Catalytic tests were performed using parallel reactor system Flowrence® from Avantium. One mixed feed gas flow was distributed over 16 channels with relative standard deviation of 2%. The mixed feed comprised about 20 vol % of $CO_2$ and 80 vol % of $H_2$. In addition about 0.5 ml/min of He was mixed with the feed as internal standard. It was aimed to have 15000 $h^{-1}$ per channel. The channels were stainless steel tubes (30 cm long with 2 µm of internal diameter) installed in a furnace. The tubes were first filled with 9.5 cm bed of coarse SiC (particle grit 40, 300 µl) in order to ensure the iso-thermal zone for the catalytic bed placement. Then 50 mg of the catalyst with a particles fraction between 150 µm and 250 µm and 50 mg were loaded. A blank test with a reactor filled with only SiC was included during every catalytic run. Prior to feeding the reaction mixture all samples were pretreated in-situ with a pure $N_2$ atmosphere for about 1 hour at about 300° C. The tubes were then pressurized to about 50 bar using a membrane based pressure controller working with $N_2$ pressure. The products were analyzed with Agilent 7890B chromatograph equipped with two loops, where one was connected to the Column 5 Haysep Q 6 Ft G3591-80013 and TCD and the second Gaspro 30M, 0.32 MM OD column followed by FID.

The conversions (X, %), space time yields (STY, $mol \cdot g_{cat}^{-1} \cdot h^{-1}$), and selectivities (S, %) are defined as follow:

$$X_{CO_2} = \left(1 - \frac{C_{He,blk} \cdot C_{CO_2,R}}{C_{He,R} \cdot C_{CO_2,blk}}\right) \cdot 100$$

$$S_i = \frac{n \cdot \left(\frac{C_{i,R}}{C_{He,R}}\right)}{\left(\frac{C_{CO_2,blk}}{C_{He,blk}} - \frac{C_{CO_2,R}}{C_{He,R}}\right)} \cdot 100$$

$$STY_i = \frac{X_{CO_2}/100 \cdot S_i/100 \cdot GHSV}{22.4}$$

where $C_{He,blk}$, $C_{He,R}$, $C_{CO_2,blk}$, $C_{CO_2,R}$ are the concentrations determined by GC analysis of He in the blank, He in the reactor effluent, $CO_2$ in the blank, and $CO_2$ in the reactor effluent, respectively, $C_{i,R}$ is the concentration the reactor effluent determined be GC analysis of a product with n carbon atoms, and GHSV is the space time velocity in $ml \cdot gcat^{-1} \cdot h^{-1}$.

Catalyst Characterization

In order to characterize the spent catalyst, the reactor with the catalyst inside was brought to a glovebox where water and oxygen levels were kept below 1 ppm and opened there to allow its transfer into a sample vial. Those precautions were taken to avoid any catalyst oxidation unrelated to $CO_2$ hydrogenation.

Nitrogen adsorption measurements. Nitrogen adsorption and desorption isotherms were recorded on a Micromeritics Asasp 2040 at 77 K. Samples were previously evacuated at about 393 K for about 10 h. The BET method was used to calculate the surface area. NLDFT method $N_2$@77-Carb Finite Pores, As=6, 2D-NLDFT method was used to calculate the pore size distribution. In@Co-1 precatalyst had a low specific surface area of about 30 m² g⁻¹ with a total pore volume of about 0.14 cm³ g⁻¹. The pore size distribution of In@Co-2 series showed that the average pore diameter was in the range of 3-6 nm with a total pore volume in the range of about 0.12-0.31 cm³ g⁻¹. The $S_{BET}$ for the In@Co-2 series was in the range of about 80-210 m² g⁻¹ with increasing of the indium content.

Scanning transmission electron microscopy (STEM) and electron energy-loss spectroscopy (EELS). Annular Dark-Field scanning transmission electron microscopy (ADF-STEM) in conjunction with Electron Energy Loss Spectroscopy (EELS) study was carried out with a Cs-Probe Corrected Titan microscope (Thermo-Fisher Scientific) which was also equipped with a GIF Quantum of model 966 from Gatan Inc. (Pleasanton, Calif.). STEM-EELS analysis was performed by operating the microscope at the accelerating voltage of 300 kV, using a convergence angle α of 17 mrad and a collection angle β of 38 mrad. Spectrum-imaging dataset included the simultaneous acquisition of zero-loss and core-loss spectra (DualEELS) using a dispersion of 0.5 eV/channel and were recorded using a beam current of 0.2 nA and a dwell time of 20 ms/pixel. The Co $L_{2,3}$-edge, In $M_{4,5}$-edge, and O K-edge were selected to build the chemical maps.

Model based quantification of EELS spectra was conducted with Gatan microscopy software 3.0. First, a thickness map was computed from the low loss spectra. In the bulk of the sample, the thickness reached a maximum value of 0.9 inelastic mean free path (IMFP or t/λ) while within the surface layer on top of nanoparticles the range of thickness was between 0.1 and 0.3 IMFPs. Thus, the effect of plural scattering had to be taken into account and was handled by forward convolution of the model using low loss spectra prior to fitting the model to the data. The model consisted of three power law backgrounds, four partial cross-sections as $\sigma_C(\beta=38$ mrad, $\Delta=100$ eV), $\sigma_{In}(\beta=38$ mrad, $\Delta=176$ eV), $\sigma_O(\beta=38$ mrad, $\Delta=100$ eV), $\sigma_{Co}(\beta=38$ mrad, $\Delta=100$ eV) calculated with the Hartree-Slater model. Indium $M_{4,5}$-edge (443 eV) and oxygen K-edge (532 eV) were treated as overlapping edges above a common background. The ELNES region was excluded during the MLLS fit since no transitions to unoccupied bound states were taken into account with the computation of Hartree-Slater cross-sections. The precision of the elemental quantification was in the order of 10% error for each element. While the accuracy of the theoretical cross-section provides 5-10% error for K-edges and 10-20% error for L-edges, it was much worse for $M_{4,5}$-edges.

In the case of In $M_{4,5}$-edge, comparison of experimental data and Hartree-Slater cross sections highlighted an overestimation by a factor 1.8 (83% error). Even considering such high error for the calculation of indium areal density, it did not change the overall picture of a surface layer highly loaded with Co and O atoms with a low amount of indium atoms.

For the In@Co solid prior to $CO_2$ hydrogenation, the specimen was prepared by mixing the samples in pure ethanol solvent and then placing 1 µl of the resultant suspension onto copper (Cu) grids having a holey-C layer of thickness of about 20 nm. Owing to the air sensitivity of In@Co solid after reaction, the sample was handled inside an Ar-filled glove box. The specimen was prepared by simply shaking a small amount of dry powder and the TEM grid inside a 2 ml sample vial. The TEM grid was retrieved and mounted in a Gatan double-tilt vacuum transfer TEM holder, model 648 that was used for the transfer into the microscope.

X-ray Photoelectron Spectroscopy (XPS). The chemical composition of the powdered samples was analyzed using high resolution X-ray photoelectron spectroscopy (XPS). XPS studies were carried out in a Kratos Axis Ultra DLD spectrometer equipped with a monochromatic Al Kα x-ray source (hv=1486.6 eV) operating at 150 W, a multichannel plate and delay line detector under a vacuum of 1~10−9 mbar. Measurements were performed in hybrid mode using electrostatic and magnetic lenses, and the take-off angle (angle between the sample surface normal and the electron optical axis of the spectrometer) was 0°. All spectra were recorded using an aperture slot of 300 µm×700 µm. The survey and high-resolution spectra were collected at fixed analyzer pass energies of 160 eV and 20 eV, respectively. Samples were mounted in floating mode in order to avoid differential charging. Charge neutralization was required for all samples. Binding energies were referenced to the C 1s peak of (C—C, C—H) bond which was set at 285.0 eV. The sample was mounted on the holder in a glovebox under controlled environment (argon) and then transferred to the XPS instrument using a transfer vessel for air-sensitive samples. The data were analyzed using commercially available software, CasaXPS.

Powder X-ray diffraction (XRD). Powder X-ray diffraction measurements were conducted using a Bruker D8 Venture single crystal diffractometer equipped with a PHOTON II area detector and an IµS microfocus source (set to 50 kV, 1 mA) providing a Mo Kα radiation ($\lambda_{K\alpha1}$=0.70930 Å, $\lambda_{K\alpha2}$=0.71359 Å). Mo X-ray radiation was used instead of the more common Cu X-ray radiation to avoid the absorption and the subsequent fluorescence of cobalt atoms. The detector was positioned at a swing angle α=55° and a sample-to-detector distance of 40 µm to collect an extended 2θ range of 2.7-107.2°. Capillaries of 1 µm diameter were filled with powders using standard procedure to handle air sensitive compound (e.g. the spent catalyst), then flame-sealed and finally mounted on the goniometer for transmission measurement. A single frame per sample was recorded with an exposure time of 10 min using a phi-360 scan (FIGS. 12A-12B). γ integration over the 5-63° 2θ range was performed by DIFFRAC.EVA software from Bruker. See FIGS. 26A-26D.

Inductively Coupled Plasma—Optical Emission Spectroscopy (ICP-OES). ICP-OES was performed using PerkinElmer Model Optima 8300 instrument. Prior to the measurement, 40 mg of a sample were digested in 8 ml of aqua regia. Microwave-assisted heating program was implemented using 15 min ramp time and 20 min hold time at 1000 W applied power and 220° C.

CHN analysis. CHN analysis was performed using Thermo Flash 2000 Organic Elemental Analyzer with the detection limits of 0.2% (w/w) for carbon, 0.1% for nitrogen and 0.08% for hydrogen.

FIGS. 27A-27D is a graphical view of catalytic activity of a) In@Co-1 catalysts with a different indium content b) In@Co-2 catalysts with a different indium content c) In@Co-1 catalysts with a different cobalt content d) In@Co-2 catalysts with a different cobalt content, according to one or more embodiments of the present disclosure.

TABLE S1

Elemental analysis (CHN and ICP-OES for In and Co) on the fresh and spent In@Co catalysts.

|  | C | H | In | Co |
|---|---|---|---|---|
| fresh | 9.2% | 3.4% | 20.2% | 46.1% |
| spent | 4.8% | 0% | 34.9% | 61.2% |

TABLE S2

Elemental surface analysis from XPS measurements.

|  | C | O | In | Co |
|---|---|---|---|---|
| fresh | 13.2% | 49.9% | 4.9% | 32% |
| spent | 24.6% | 20.4% | 8.3% | 36.7% |

TABLE S3

$CO_2$ conversion and selectivities to different products over individual oxides and In@Co systems prepared by alternative methods (Reaction conditions are 300° C., 50 bar, 20% $H_2$ 80% $CO_2$ feed, 50 mg of catalyst, 34.9 wt % In, WHSV 2)

|  | $CO_2$ conversion/% | CO selectivity/% | $CH_4$ selectivity/% | Methanol selectivity/% |
|---|---|---|---|---|
| In@Co-1 | 19 | 23 | 8 | 69 |
| In@Co-2 | 16 | 21 | 4 | 75 |

TABLE S3-continued $CO_2$ conversion and selectivities to different products over individual oxides and In@Co systems prepared by alternative methods (Reaction conditions are 300° C., 50 bar, 20% $H_2$ 80% $CO_2$ feed, 50 mg of catalyst, 34.9 wt % In, WHSV 2)

| | $CO_2$ conversion/% | CO selectivity/% | $CH_4$ selectivity/% | Methanol selectivity/% |
|---|---|---|---|---|
| $In_2O_3$ | 1 | 100 | 0 | 0 |
| $Co_3O_4$ [a] | 80 | 0 | 100 | 0 |
| In@Co by iwi | 3 | 10 | 60 | 30 |
| In@Co by ball milling | 6 | 50 | 25 | 25 |
| $Co_3InC_{0.75}$ | 3 | 94 | 6 | 0 |
| 50% $Co_3InC_{0.75}$ + 50% $In_2O_3$ | 1.7 | 96 | 4 | 0 |
| 20% $Co_3InC_{0.75}$ + 80% $In_2O_3$ | 2.1 | 97 | 3 | 0 |
| 80% $Co_3InC_{0.75}$ + 20% $In_2O_3$ | 4.2 | 96 | 4 | 0 |

[a] $CoO + Co^0$ after the reaction

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto Various examples have been described. These and other examples are within the scope of the following claims.

What is claimed is:

1. A pre-catalyst, comprising:
both of indium hydroxide and indium oxyhydroxide mixed with an active oxide and carbon source;
wherein the active oxide includes a mixed valence metal oxide.

2. The pre-catalyst of claim 1, wherein the active oxide is a reducible oxide.

3. The pre-catalyst of claim 1, wherein the active oxide includes one or more of cobalt, nickel, copper, manganese, iron, and vanadium.

4. The pre-catalyst of claim 1, further comprising a refractory oxide.

5. The pre-catalyst of claim 4, wherein the refractory oxide includes one or more of zirconium dioxide ($ZrO_2$), silica ($SiO_2$), alumina ($Al_2O_3$), gallium oxide ($Ga_2O_3$), cerium oxide ($CeO_2$), vanadium oxide ($V_2O_5$), chromium oxide ($Cr_2O_3$), titanium dioxide ($TiO_2$), magnesium oxide (MgO), zinc oxide (ZnO), tin oxide ($SnO_2$), and carbon black (C).

6. The pre-catalyst of claim 1, wherein a form of the catalyst is one or more of extrudates, granules, spheres, monoliths, particles, and pellets.

7. The catalyst of claim 1, wherein the catalyst further comprises one or more of lubricants, peptizers, plasticizers, porogens, binders, and fillers.

8. The pre-catalyst of claim 1, wherein the pre-catalyst includes the carbon source and wherein the carbon source is a carbonate.

9. The pre-catalyst of claim 1, wherein the pre-catalyst includes the active oxide and wherein the active oxide includes nanoparticles.

10. The pre-catalyst of claim 1, wherein the pre-catalyst includes indium hydroxide and the active oxide, and wherein the active oxide is $Co_3O_4$, and wherein the indium hydroxide is supported on the active oxide.

* * * * *